US007358408B2

(12) United States Patent
Rahman et al.

(10) Patent No.: US 7,358,408 B2
(45) Date of Patent: *Apr. 15, 2008

(54) PHOTOACTIVE COMPOUNDS

(75) Inventors: M. Dalil Rahman, Flemington, NJ (US); Francis M. Houlihan, Millington, NJ (US)

(73) Assignee: AZ Electronic Materials USA Corp., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/439,753

(22) Filed: May 16, 2003

(65) Prior Publication Data

US 2004/0229155 A1 Nov. 18, 2004

(51) Int. Cl.
*C07C 13/00* (2006.01)
(52) U.S. Cl. ...................................... 585/24
(58) Field of Classification Search ............... 585/24
See application file for complete search history.

(56) References Cited

U.S. PATENT DOCUMENTS

| | | | |
|---|---|---|---|
| 5,021,197 A | 6/1991 | Takeda et al. | |
| 5,159,088 A | 10/1992 | Schwalm | |
| 5,399,596 A | 3/1995 | Kouge et al. | |
| 5,798,396 A | 8/1998 | Takahashi et al. | |
| 5,837,420 A * | 11/1998 | Aoai et al. | 430/270.1 |
| 6,365,322 B1 * | 4/2002 | Padmanaban et al. | 430/270.1 |
| 6,528,229 B2 * | 3/2003 | Sato | 430/170 |
| 6,733,951 B2 * | 5/2004 | Kodama | 430/270.1 |
| 6,749,986 B2 * | 6/2004 | Taylor et al. | 430/270.1 |
| 6,749,987 B2 * | 6/2004 | Kodama et al. | 430/270.1 |
| 6,808,862 B2 * | 10/2004 | Kodama | 430/270.1 |
| 6,844,132 B2 * | 1/2005 | Kodama et al. | 430/270.1 |
| 6,858,370 B2 * | 2/2005 | Kodama et al. | 430/270.1 |
| 6,927,009 B2 * | 8/2005 | Kodama et al. | 430/270.1 |
| 6,991,888 B2 * | 1/2006 | Padmanaban et al. | 430/270.1 |
| 2001/0036591 A1 | 11/2001 | Schulz et al. | |
| 2002/0076643 A1 * | 6/2002 | Ohsawa et al. | 430/270.1 |
| 2002/0090571 A1 * | 7/2002 | Oomori et al. | 430/270.1 |
| 2003/0194650 A1 * | 10/2003 | Kanna et al. | 430/285.1 |
| 2005/0130060 A1 * | 6/2005 | Kodama et al. | 430/270.1 |

FOREIGN PATENT DOCUMENTS

| | | | |
|---|---|---|---|
| CA | 2299856 | | 9/2000 |
| EP | 0 331 988 A1 | | 9/1989 |
| EP | 0 393 893 A1 | | 10/1990 |
| EP | 0 972 761 | * | 1/2000 |
| EP | 1 033 624 | * | 9/2000 |
| EP | 1 033 624 A | | 9/2000 |
| EP | 1 035 105 A | | 9/2000 |
| JP | 63-008365 | | 1/1988 |
| JP | 64-083029 | | 3/1989 |
| JP | 64-083060 | | 3/1989 |
| JP | 01-290658 | | 11/1989 |
| JP | 02-272081 | | 11/1990 |
| JP | 03-017101 | | 1/1991 |
| JP | 03-048654 | | 3/1991 |
| JP | 03-059001 | | 3/1991 |
| JP | 03-200761 | | 9/1991 |
| JP | 3-0290287 | | 12/1991 |
| JP | 4-11625 | | 1/1992 |
| JP | 05-230189 | | 9/1993 |
| JP | 07-278273 | | 10/1995 |
| JP | 08-188570 | | 7/1996 |
| JP | 08-245764 | | 9/1996 |
| JP | 08-245765 | | 9/1996 |
| JP | 09 045134 | | 2/1997 |
| WO | 02/19033 | * | 3/2002 |
| WO | WO 02/19033 A | | 3/2002 |
| WO | WO 02/079338 A2 | | 10/2002 |
| WO | WO 03/107093 A | | 12/2003 |

OTHER PUBLICATIONS

PTO Search Report, Oct. 30, 2007.*
Communication pursuant to Article 96(2) EPC dated Dec. 20, 2006 for EP Application No. 04 731 596.5.
Office Action from Chinese Patent Office, and English translation thereof, for Chinese Patent Application No. 200480013376.0 which corresponds to the present application, Mar. 23, 2007.
E. A. Bartmann, Eine einfache und allgemeine Methode zur hertsellung von alpha-Disulfonen (R1SO2SO2R2) ; SYNTHESIS, vol. 5, pp. 490-496, XP-001184002, 1993.
M. Shirai et al., "Photoacid and photobase generators: chemistry and applications to polymeric materials", Progress in Polymer Science, vol. 21, pp. 1-45, XP-002299394, 1996.

* cited by examiner

*Primary Examiner*—Hoa Van Le
(74) *Attorney, Agent, or Firm*—Alan P. Kass

(57) ABSTRACT

The present invention relates to a novel photoactive compounds that can be used in formulating photoresist compositions.

1 Claim, No Drawings

PHOTOACTIVE COMPOUNDS

FIELD OF INVENTION

The present invention relates to a novel photoactive compounds useful in photoresist compositions in the field of microlithography, and especially useful for imaging negative and positive patterns in the production of semiconductor devices, as well as photoresist compositions and processes for imaging photoresists.

BACKGROUND OF THE INVENTION

Photoresist compositions are used in microlithography processes for making miniaturized electronic components such as in the fabrication of computer chips and integrated circuits. Generally, in these processes, a thin coating of film of a photoresist composition is first applied to a substrate material, such as silicon wafers used for making integrated circuits. The coated substrate is then baked to evaporate any solvent in the photoresist composition and to fix the coating onto the substrate. The photoresist coated on the substrate is next subjected to an image-wise exposure to radiation.

The radiation exposure causes a chemical transformation in the exposed areas of the coated surface. Visible light, ultraviolet (UV) light, electron beam and X-ray radiant energy are radiation types commonly used today in microlithographic processes. After this image-wise exposure, the coated substrate is treated with a developer solution to dissolve and remove either the radiation exposed or the unexposed areas of the photoresist. The trend toward the miniaturization of semiconductor devices has led to the use of new photoresists that are sensitive at lower and lower wavelengths of radiation and has also led to the use of sophisticated multilevel systems to overcome difficulties associated with such miniaturization.

There are two types of photoresist compositions: negative-working and positive-working. The type of photoresist used at a particular point in lithographic processing is determined by the design of the semiconductor device. When negative-working photoresist compositions are exposed image-wise to radiation, the areas of the photoresist composition exposed to the radiation become less soluble to a developer solution (e.g. a cross-linking reaction occurs) while the unexposed areas of the photoresist coating remain relatively soluble to such a solution. Thus, treatment of an exposed negative-working resist with a developer causes removal of the non-exposed areas of the photoresist coating and the creation of a negative image in the coating, thereby uncovering a desired portion of the underlying substrate surface on which the photoresist composition was deposited.

On the other hand, when positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus, treatment of an exposed positive-working photoresist with the developer causes removal of the exposed areas of the coating and the creation of a positive image in the photoresist coating. Again, a desired portion of the underlying surface is uncovered.

Photoresist resolution is defined as the smallest feature, which the resist composition can transfer from the photomask to the substrate with a high degree of image edge acuity after exposure and development. In many leading edge manufacturing applications today, photoresist resolution on the order of less than one-half micron are necessary. In addition, it is almost always desirable that the developed photoresist wall profiles be near vertical relative to the substrate. Such demarcations between developed and undeveloped areas of the resist coating translate into accurate pattern transfer of the mask image onto the substrate. This becomes even more critical as the push toward miniaturization reduces the critical dimensions on the devices. In cases where the photoresist dimensions have been reduced to below 150 nm, the roughness of the photoresist patterns has become a critical issue. Edge roughness, commonly known as line edge roughness, is typically observed for line and space patterns as roughness along the photoresist line, and for contact holes as side wall roughness. Edge roughness can have adverse effects on the lithographic performance of the photoresist, especially in reducing the critical dimension latitude and also in transferring the line edge roughness of the photoresist to the substrate. Hence, photoresists that minimize edge roughness are highly desirable.

Photoresists sensitive to short wavelengths, between about 100 nm and about 300 nm are often used where subhalfmicron geometries are required. Particularly preferred are photoresists comprising non-aromatic polymers, a photoacid generator, optionally a dissolution inhibitor, and solvent.

High resolution, chemically amplified, deep ultraviolet (100-300 nm) positive and negative tone photoresists are available for patterning images with less than quarter micron geometries. To date, there are three major deep ultraviolet (UV) exposure technologies that have provided significant advancement in miniaturization, and these use lasers that emit radiation at 248 nm, 193 nm and 157 nm. Photoresists used in the deep UV typically comprise a polymer which has an acid labile group and which can deprotect in the presence of an acid, a photoactive component which generates an acid upon absorption of light, and a solvent.

Photoresists for 248 nm have typically been based on substituted polyhydroxystyrene and its copolymers, such as those described in U.S. Pat. Nos. 4,491,628 and 5,350,660. On the other hand, photoresists for 193 nm exposure require non-aromatic polymers, since aromatics are opaque at this wavelength. U.S. Pat. No. 5,843,624 and GB 2,320,718 disclose photoresists useful for 193 nm exposure. Generally, polymers containing alicyclic hydrocarbons are used for photoresists for exposure below 200 nm. Alicyclic hydrocarbons are incorporated into the polymer for many reasons, primarily since they have relatively high carbon:hydrogen ratios which improve etch resistance, they also provide transparency at low wavelengths and they have relatively high glass transition temperatures. Photoresists sensitive at 157 nm have been based on fluorinated polymers, which are known to be substantially transparent at that wavelength. Photoresists derived from polymers containing fluorinated groups are described in WO 00/67072 and WO 00/17712.

The polymers used in a photoresist are designed to be transparent to the imaging wavelength, but on the other hand, the photoactive component has been typically designed to be absorbing at the imaging wavelength to maximize photosensitivity. The photosensitivity of the photoresist is dependent on the absorption characteristics of the photoactive component, the higher the absorption, the less the energy required to generate the acid, and the more photosensitive is the photoresist.

SUMMARY OF THE INVENTION

The present invention relates to a compound of the formula

Y—Ar where Ar is selected from

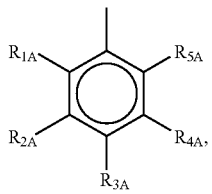

naphthyl, or anthryl;

Y is selected from

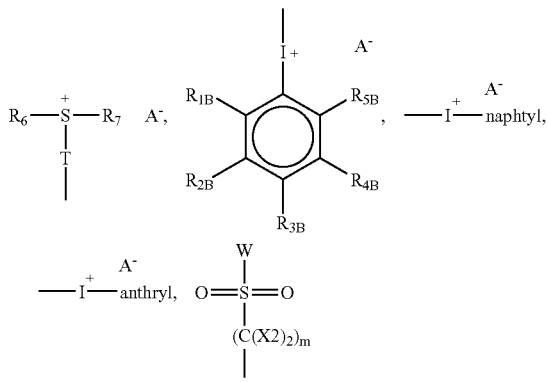

where W is selected from

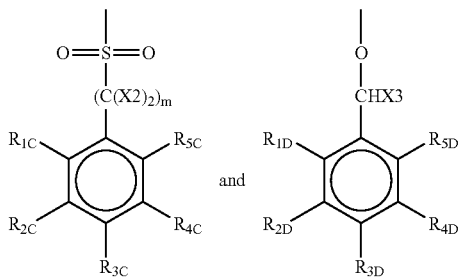

$R_{1A}$, $R_{1B}$, $R_{1C}$, $R_{2A}$, $R_{2B}$, $R_{2C}$, $R_{2D}$, $R_{3A}$, $R_{3B}$, $R_{3C}$, $R_{3D}$, $R_{4A}$, $R_{4B}$, $R_{4C}$, $R_{4D}$, $R_{5A}$, $R_{5B}$ and $R_{5C}$, are each independently selected from Z, hydrogen, $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, arylcarbonylmethylene group, $C_{1-20}$ straight or branched alkoxy chain, nitro, cyano, tresyl, or hydroxyl; either (i) one of $R_{1D}$ or $R_{5D}$ is nitro with the other being selected from hydrogen, $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, arylcarbonylmethylene group, cyano, or hydroxyl or (ii) both of $R_{1D}$ and $R_{5D}$ are nitro; $R_6$ and $R_7$ are each independently selected from $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, arylcarbonylmethylene group, nitro, cyano, or hydroxyl or $R_6$ and $R_7$ together with the S atom to which they are attached form a 5-, 6-, or 7-membered saturated or unsaturated ring optionally containing one or more O atoms which can be unsubstituted or substituted; T is a direct bond, a divalent $C_{1-20}$ straight or branched alkyl group optionally containing one or more O atoms, divalent $C_{5-50}$ aryl group, divalent $C_{5-50}$ aralkyl group, or divalent $C_{5-50}$ monocyclic, bicyclic or tricyclic alkyl group; Z is —$(V)_j$—$(C(X11)(X12))_n$—O—C(=O)—$R_8$, where either (i) one of X11 or X12 is $C_{1-20}$ straight or branched alkyl chain containing at least one fluorine atom and the other is hydrogen, halogen, or $C_{1-20}$ straight or branched alkyl chain or (ii) both of X11 and X12 are $C_{1-20}$ straight or branched alkyl chain containing at least one fluorine atom; V is a linkage group selected from a direct bond, a divalent $C_{1-20}$ straight or branched alkyl group optionally containing one or more O atoms, divalent $C_{5-50}$ aryl group, divalent $C_{5-50}$ aralkyl group, or divalent $C_{5-50}$ monocyclic, bicyclic or tricyclic alkyl group; X2 is hydrogen, halogen, or $C_{1-20}$ straight or branched alkyl chain optionally containing one or more O atoms; $R_8$ is a $C_{1-20}$ straight or branched alkyl chain optionally containing one or more O atoms, a $C_{5-50}$ monocyclic, bicyclic, or tricyclic alkyl group, or a $C_{5-50}$ aryl group; X3 is hydrogen, $C_{1-20}$ straight or branched alkyl chain, halogen, cyano, or —C(=O)—$R_{50}$ where $R_{50}$ is selected from $C_{1-20}$ straight or branched alkyl chain optionally containing one or more O atoms or —O—$R_{51}$ where $R_{51}$ is hydrogen or $C_{1-20}$ straight or branched alkyl chain; j is 0 to 10; m is 0 to 10; and n is 0 to 10, the $C_{1-20}$ straight or branched alkyl chain optionally containing one or more O atoms, $C_{1-20}$ straight or branched alkyl chain, $C_{1-20}$ straight or branched alkoxy chain, $C_{5-50}$ monocyclic, bicyclic, or tricyclic alkyl group, $C_{5-50}$ cyclic alkylcarbonyl group, $C_{5-50}$ aralkyl group, $C_{5-50}$ aryl group, naphthyl, anthryl, 5-, 6-, or 7-membered saturated or unsaturated ring optionally containing one or more O atoms, or arylcarbonylmethylene group being unsubstituted or substituted by one or more groups selected from the group consisting of Z, halogen, $C_{1-20}$ alkyl, $C_{3-20}$ cyclic alkyl, $C_{1-20}$ alkoxy, $C_{3-20}$ cyclic alkoxy, di $C_{1-20}$ alkylamino, dicyclic di $C_{1-20}$ alkylamino, hydroxyl, cyano, nitro, tresyl, oxo, aryl, aralkyl, oxygen atom, $CF_3SO_3$, aryloxy, arylthio, and groups of formulae (II) to (VI):

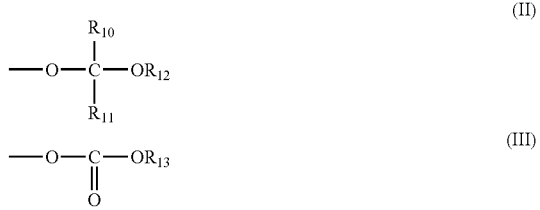

-continued

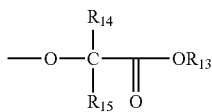
(IV)

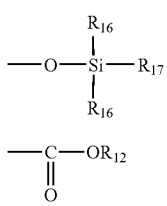
(V)

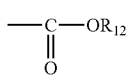
(VI)

$R_{10}$ and $R_{11}$ each independently represent a hydrogen atom, a $C_{1-20}$ straight or branched alkyl chain optionally containing one or more O atoms, or a $C_{5-50}$ monocyclic, bicyclic, or tricyclic alkyl group, or $R_{10}$ and $R_{11}$ together can represent an alkylene group to form a five- or six-membered ring, $R_{12}$ represents a $C_{1-20}$ straight or branched alkyl chain optionally containing one or more O atoms, a $C_{5-50}$ monocyclic, bicyclic, or tricyclic alkyl group, or a $C_{5-50}$ aralkyl group, or $R_{10}$ and $R_{12}$ together represent an alkylene group which forms a five- or six-membered ring together with the interposing —C—O— group, the carbon atom in the ring being optionally substituted by an oxygen atom, $R_{13}$ represents a $C_{1-20}$ straight or branched alkyl chain optionally containing one or more O atoms or a $C_{5-50}$ monocyclic, bicyclic, or tricyclic alkyl group, $R_{14}$ and $R_{15}$ each independently represent a hydrogen atom, a $C_{1-20}$ straight or branched alkyl chain optionally containing one or more O atoms or a $C_{5-50}$ monocyclic, bicyclic, or tricyclic alkyl group, $R_{16}$ represents a $C_{1-20}$ straight or branched alkyl chain optionally containing one or more O atoms, a $C_{5-50}$ monocyclic, bicyclic, or tricyclic alkyl group, a $C_{5-50}$ aryl group, or a $C_{5-50}$ aralkyl group, and $R_{17}$ represents $C_{1-20}$ straight or branched alkyl chain optionally containing one or more O atoms, a $C_{5-50}$ monocyclic, bicyclic, or tricyclic alkyl group, a $C_{5-50}$ aryl group, a $C_{5-50}$ aralkyl group, the group —Si$(R_{16})_2R_{17}$, or the group —O—Si$(R_{16})_2R_{17}$, the $C_{1-20}$ straight or branched alkyl chain optionally containing one or more O atoms, $C_{5-50}$ monocyclic, bicyclic, or tricyclic alkyl group, $C_{5-50}$ aryl group, and $C_{5-50}$ aralkyl group being unsubstituted or substituted as above; and $A^-$ is an anion.

In certain embodiments, Ar is

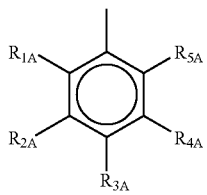

and Y is

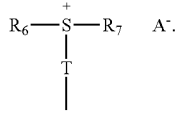

In other embodiments, $R_6$ and $R_7$ are each independently selected from $C_{1-20}$ straight or branched alkyl chain optionally containing one or more O atoms or $C_{5-50}$ aryl group and each of $R_{1A}$, $R_{2A}$, $R_{3A}$, $R_{4A}$, and $R_{5A}$ are independently selected from Z, hydrogen, or $C_{1-20}$ straight or branched alkyl chain optionally containing one or more O atoms, the $C_{1-20}$ straight or branched alkyl chain optionally containing one or more O atoms or $C_{5-50}$ aryl group being unsubstituted or substituted.

In further embodiments, either one of $R_{1A}$, $R_{2A}$, $R_{3A}$, $R_{4A}$, or $R_{5A}$ is Z.

In further embodiments, $R_6$ and $R_7$ are each independently $C_{1-20}$ straight or branched alkyl chain optionally containing one or more O atoms, $R_3A$ is Z and either each of $R_{1A}$, $R_{2A}$, $R_{4A}$, and $R_{5A}$ are hydrogen;

each of $R_{1A}$, $R_{2A}$, and $R_{4A}$ are hydrogen and $R_{5A}$ is $C_{1-20}$ straight or branched alkyl chain optionally containing one or more O atoms;

each of $R_{1A}$, $R_{2A}$, and $R_5A$ are hydrogen and $R_{4A}$ is $C_{1-20}$ straight or branched alkyl chain optionally containing one or more O atoms;

each of $R_{1A}$, $R_{4A}$, and $R_{5A}$ are hydrogen and $R_{2A}$ is $C_{1-20}$ straight or branched alkyl chain optionally containing one or more O atoms;

each of $R_{2A}$, $R_{4A}$, and $R_{5A}$ are hydrogen and $R_{1A}$ is $C_{1-20}$ straight or branched alkyl chain optionally containing one or more O atoms;

each of $R_{4A}$ and $R_{5A}$ are hydrogen and $R_{1A}$ and $R_{2A}$ are $C_{1-20}$ straight or branched alkyl chain optionally containing one or more O atoms;

each of $R_{2A}$ and $R_{5A}$ are hydrogen and $R_{1A}$ and $R_{4A}$ are $C_{1-20}$ straight or branched alkyl chain optionally containing one or more O atoms;

each of $R_{2A}$ and $R_{4A}$ are hydrogen and $R_{1A}$ and $R_{5A}$ are $C_{1-20}$ straight or branched alkyl chain optionally containing one or more O atoms;

each of $R_{1A}$ and $R_{5A}$ are hydrogen and $R_{2A}$ and $R_{4A}$ are $C_{1-20}$ straight or branched alkyl chain optionally containing one or more O atoms;

each of $R_{1A}$ and $R_{4A}$ are hydrogen and $R_{2A}$ and $R_{5A}$ are $C_{1-20}$ straight or branched alkyl chain optionally containing one or more O atoms;

each of $R_{1A}$ and $R_{2A}$ are hydrogen and $R_{4A}$ and $R_{5A}$ are $C_{1-20}$ straight or branched alkyl chain optionally containing one or more O atoms;

$R_{5A}$ is hydrogen and $R_{1A}$, $R_{2A}$ and $R_{4A}$ are $C_{1-20}$ straight or branched alkyl chain optionally containing one or more O atoms;

$R_{4A}$ is hydrogen and $R_{1A}$, $R_{2A}$ and $R_{5A}$ are $C_{1-20}$ straight or branched alkyl chain optionally containing one or more O atoms;

$R_{2A}$ is hydrogen and $R_{1A}$, $R_{4A}$ and $R_{5A}$ are $C_{1-20}$ straight or branched alkyl chain optionally containing one or more O atoms;

$R_{1A}$ is hydrogen and $R_{2A}$, $R_{4A}$ and $R_{5A}$ are $C_{1-20}$ straight or branched alkyl chain optionally containing one or more O atoms; or each of $R_{1A}$, $R_{2A}$, $R_{4A}$, and $R_{5A}$ are $C_{1-20}$ straight or branched alkyl chain optionally containing one or more O atoms, where the $C_{1-20}$ straight or branched alkyl chain optionally containing one or more O atoms is unsubstituted or substituted.

In further embodiments, $R_6$ and $R_7$ are each independently $C_{5-50}$ aryl group, $R_{3A}$ is Z and either each of $R_{1A}$, $R_{2A}$, $R_{4A}$, and $R_{5A}$ are hydrogen;

each of $R_{1A}$, $R_{2A}$, and $R_{4A}$ are hydrogen and $R_{5A}$ is $C_{1-20}$ straight or branched alkyl chain optionally containing one or more O atoms;

each of $R_{1A}$, $R_{2A}$, and $R_{5A}$ are hydrogen and $R_{4A}$ is $C_{1-20}$ straight or branched alkyl chain optionally containing one or more O atoms;

each of $R_{1A}$, $R_{4A}$, and $R_{5A}$ are hydrogen and $R_{2A}$ is $C_{1-20}$ straight or branched alkyl chain optionally containing one or more O atoms;

each of $R_{2A}$, $R_{4A}$, and $R_{5A}$ are hydrogen and $R_{1A}$ is $C_{1-20}$ straight or branched alkyl chain optionally containing one or more O atoms;

each of $R_{4A}$ and $R_{5A}$ are hydrogen and $R_{1A}$ and $R_{2A}$ are $C_{1-20}$ straight or branched alkyl chain optionally containing one or more O atoms;

each of $R_{2A}$ and $R_{5A}$ are hydrogen and $R_{1A}$ and $R_{4A}$ are $C_{1-20}$ straight or branched alkyl chain optionally containing one or more O atoms;

each of $R_{2A}$ and $R_{4A}$ are hydrogen and $R_{1A}$ and $R_{5A}$ are $C_{1-20}$ straight or branched alkyl chain optionally containing one or more O atoms;

each of $R_{1A}$ and $R_{5A}$ are hydrogen and $R_{2A}$ and $R_{4A}$ are $C_{1-20}$ straight or branched alkyl chain optionally containing one or more O atoms;

each of $R_{1A}$ and $R_{4A}$ are hydrogen and $R_{2A}$ and $R_{5A}$ are $C_{1-20}$ straight or branched alkyl chain optionally containing one or more O atoms;

each of $R_{1A}$ and $R_{2A}$ are hydrogen and $R_{4A}$ and $R_{5A}$ are $C_{1-20}$ straight or branched alkyl chain optionally containing one or more O atoms;

$R_{5A}$ is hydrogen and $R_{1A}$, $R_{2A}$ and $R_{4A}$ are $C_{1-20}$ straight or branched alkyl chain optionally containing one or more O atoms;

$R_{4A}$ is hydrogen and $R_{1A}$, $R_{2A}$ and $R_{5A}$ are $C_{1-20}$ straight or branched alkyl chain optionally containing one or more O atoms;

$R_{2A}$ is hydrogen and $R_{1A}$, $R_{4A}$ and $R_{5A}$ are $C_{1-20}$ straight or branched alkyl chain optionally containing one or more O atoms;

$R_{1A}$ is hydrogen and $R_{2A}$, $R_{4A}$ and $R_{5A}$ are $C_{1-20}$ straight or branched alkyl chain optionally containing one or more O atoms; or each of $R_{1A}$, $R_{2A}$, $R_{4A}$, and $R_{5A}$ are $C_{1-20}$ straight or branched alkyl chain optionally containing one or more O atoms, where the $C_{1-20}$ straight or branched alkyl chain optionally containing one or more O atoms is unsubstituted or substituted.

In other embodiments, Ar is

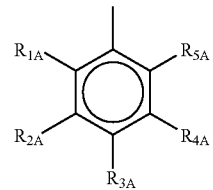

and Y is

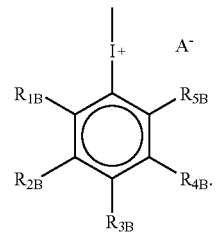

In further embodiments, either one of $R_{1B}$, $R_{2B}$, $R_{3B}$, $R_{4B}$, or $R_{5B}$ is Z or hydrogen.

In further embodiments, $R_{3A}$ is Z and either each of $R_{1A}$, $R_{2A}$, $R_{4A}$, and $R_{5A}$ are hydrogen;

each of $R_{1A}$, $R_{2A}$, and $R_{4A}$ are hydrogen and $R_{5A}$ is $C_{1-20}$ straight or branched alkyl chain optionally containing one or more O atoms;

each of $R_{1A}$, $R_{2A}$, and $R_{5A}$ are hydrogen and $R_{4A}$ is $C_{1-20}$ straight or branched alkyl chain optionally containing one or more O atoms;

each of $R_{1A}$, $R_{4A}$, and $R_{5A}$ are hydrogen and $R_{2A}$ is $C_{1-20}$ straight or branched alkyl chain optionally containing one or more O atoms;

each of $R_{2A}$, $R_{4A}$, and $R_{5A}$ are hydrogen and $R_{1A}$ is $C_{1-20}$ straight or branched alkyl chain optionally containing one or more O atoms;

each of $R_{4A}$ and $R_{5A}$ are hydrogen and $R_{1A}$ and $R_{2A}$ are $C_{1-20}$ straight or branched alkyl chain optionally containing one or more O atoms;

each of $R_{2A}$ and $R_{5A}$ are hydrogen and $R_{1A}$ and $R_{4A}$ are $C_{1-20}$ straight or branched alkyl chain optionally containing one or more O atoms;

each of $R_{2A}$ and $R_{4A}$ are hydrogen and $R_{1A}$ and $R_{5A}$ are $C_{1-20}$ straight or branched alkyl chain optionally containing one or more O atoms;

each of $R_{1A}$ and $R_{5A}$ are hydrogen and $R_{2A}$ and $R_{4A}$ are $C_{1-20}$ straight or branched alkyl chain optionally containing one or more O atoms;

each of $R_{1A}$ and $R_{4A}$ are hydrogen and $R_{2A}$ and $R_{5A}$ are $C_{1-20}$ straight or branched alkyl chain optionally containing one or more O atoms;

each of $R_{1A}$ and $R_{2A}$ are hydrogen and $R_{4A}$ and $R_{5A}$ are $C_{1-20}$ straight or branched alkyl chain optionally containing one or more O atoms;

$R_{5A}$ is hydrogen and $R_{1A}$, $R_{2A}$ and $R_{4A}$ are $C_{1-20}$ straight or branched alkyl chain optionally containing one or more O atoms;

$R_{4A}$ is hydrogen and $R_{1A}$, $R_{2A}$ and $R_{5A}$ are $C_{1-20}$ straight or branched alkyl chain optionally containing one or more O atoms;

$R_{2A}$ is hydrogen and $R_{1A}$, $R_{4A}$ and $R_{5A}$ are $C_{1-20}$ straight or branched alkyl chain optionally containing one or more O atoms;

$R_{1A}$ is hydrogen and $R_{2A}$, $R_{4A}$ and $R_{5A}$ are $C_{1-20}$ straight or branched alkyl chain optionally containing one or more O atoms; or each of $R_{1A}$, $R_{2A}$, $R_{4A}$, and $R_{5A}$ are $C_{1-20}$ straight or branched alkyl chain optionally containing one or more O atoms, wherein the $C_{1-20}$ straight or branched alkyl chain optionally containing one or more O atoms is unsubstituted or substituted.

In further embodiments, $R_{3B}$ is Z or hydrogen and either each of $R_{1B}$, $R_{2B}$, $R_{4B}$, and $R_{5B}$ are hydrogen;

each of $R_{1B}$, $R_{2B}$, and $R_{4B}$ are hydrogen and $R_{5B}$ is $C_{1-20}$ straight or branched alkyl chain optionally containing one or more O atoms;

each of $R_{1B}$, $R_{2B}$, and $R_{5B}$ are hydrogen and $R_{4B}$ is $C_{1-20}$ straight or branched alkyl chain optionally containing one or more O atoms;

each of $R_{1B}$, $R_{4B}$, and $R_{5B}$ are hydrogen and $R_{2B}$ is $C_{1-20}$ straight or branched alkyl chain optionally containing one or more O atoms;

each of $R_{2B}$, $R_{4B}$, and $R_{5B}$ are hydrogen and $R_{1B}$ is $C_{1-20}$ straight or branched alkyl chain optionally containing one or more O atoms;

each of $R_{4B}$ and $R_{5B}$ are hydrogen and $R_{1B}$ and $R_{2B}$ are $C_{1-20}$ straight or branched alkyl chain optionally containing one or more O atoms;

each of $R_{2B}$ and $R_{5B}$ are hydrogen and $R_{1B}$ and $R_{4B}$ are $C_{1-20}$ straight or branched alkyl chain optionally containing one or more O atoms;

each of $R_{2B}$ and $R_{4B}$ are hydrogen and $R_{1B}$ and $R_{5B}$ are $C_{1-20}$ straight or branched alkyl chain optionally containing one or more O atoms;

each of $R_{1B}$ and $R_{5B}$ are hydrogen and $R_{2B}$ and $R_{4B}$ are $C_{1-20}$ straight or branched alkyl chain optionally containing one or more O atoms;

each of $R_{1B}$ and $R_{4B}$ are hydrogen and $R_{2B}$ and $R_{5B}$ are $C_{1-20}$ straight or branched alkyl chain optionally containing one or more O atoms;

each of $R_{1B}$ and $R_{2B}$ are hydrogen and $R_{4B}$ and $R_{5B}$ are $C_{1-20}$ straight or branched alkyl chain optionally containing one or more O atoms;

$R_{5B}$ is hydrogen and $R_{1B}$, $R_{2B}$ and $R_{4B}$ are $C_{1-20}$ straight or branched alkyl chain optionally containing one or more O atoms;

$R_{4B}$ is hydrogen and $R_{1B}$, $R_{2B}$ and $R_{5B}$ are $C_{1-20}$ straight or branched alkyl chain optionally containing one or more O atoms;

$R_{2B}$ is hydrogen and $R_{1B}$, $R_{4B}$ and $R_{5B}$ are $C_{1-20}$ straight or branched alkyl chain optionally containing one or more O atoms;

$R_{1B}$ is hydrogen and $R_{2B}$, $R_{4B}$ and $R_{5B}$ are $C_{1-20}$ straight or branched alkyl chain optionally containing one or more O atoms; or each of $R_{1B}$, $R_{2B}$, $R_{4B}$, and $R_{5B}$ are $C_{1-20}$ straight or branched alkyl chain optionally containing one or more O atoms, where the $C_{1-20}$ straight or branched alkyl chain optionally containing one or more O atoms is unsubstituted or substituted.

In other embodiments, Ar is

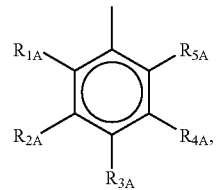

Y is

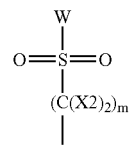

and W is

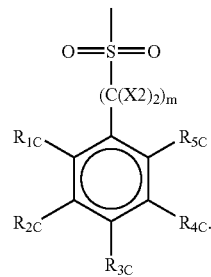

Further embodiments include those where $R_{3A}$ is Z and $R_{1A}$, $R_{2A}$, $R_{4A}$, and $R_{5A}$ are as described above. In further embodiments, X2 is selected from hydrogen, methyl or perfluoromethyl and m is 1. In further embodiments, $R_{3C}$ is Z or hydrogen with either each of $R_{1C}$, $R_{4C}$, and $R_{5C}$ are hydrogen and $R_{2C}$ is $C_{1-20}$ straight or branched alkyl chain optionally containing one or more O atoms;

each of $R_{2C}$, $R_{4C}$, and $R_{5C}$ are hydrogen and $R_{1C}$ is $C_{1-20}$ straight or branched alkyl chain optionally containing one or more O atoms;

each of $R_{4C}$ and $R_{5C}$ are hydrogen and $R_{1C}$ and $R_{2C}$ are $C_{1-20}$ straight or branched alkyl chain optionally containing one or more O atoms;

each of $R_{2C}$ and $R_{5C}$ are hydrogen and $R_{1C}$ and $R_{4C}$ are $C_{1-20}$ straight or branched alkyl chain optionally containing one or more O atoms;

each of $R_{2C}$ and $R_{4C}$ are hydrogen and $R_{1C}$ and $R_{5C}$ are $C_{1-20}$ straight or branched alkyl chain optionally containing one or more O atoms;

each of $R_{1C}$ and $R_{5C}$ are hydrogen and $R_{2C}$ and $R_{4C}$ are $C_{1-20}$ straight or branched alkyl chain optionally containing one or more O atoms;

each of $R_{1C}$ and $R_{4C}$ are hydrogen and $R_{2C}$ and $R_{5C}$ are $C_{1-20}$ straight or branched alkyl chain optionally containing one or more O atoms;

each of $R_{1C}$ and $R_{2C}$ are hydrogen and $R_{4C}$ and $R_{5C}$ are $C_{1-20}$ straight or branched alkyl chain optionally containing one or more O atoms;

$R_{5C}$ is hydrogen and $R_{1C}$, $R_{2C}$ and $R_{4C}$ are $C_{1-20}$ straight or branched alkyl chain optionally containing one or more O atoms;

$R_{4C}$ is hydrogen and $R_{1C}$, $R_{2C}$ and $R_{5C}$ are $C_{1-20}$ straight or branched alkyl chain optionally containing one or more O atoms;

$R_{2C}$ is hydrogen and $R_{1C}$, $R_{4C}$ and $R_{5C}$ are $C_{1-20}$ straight or branched alkyl chain optionally containing one or more O atoms;

$R_{1C}$ is hydrogen and $R_{2C}$, $R_{4C}$ and $R_{5C}$ are $C_{1-20}$ straight or branched alkyl chain optionally containing one or more O atoms; or each of $R_{1C}$, $R_{2C}$, $R_{4C}$, and $R_{5C}$ are $C_{1-20}$ straight or branched alkyl chain optionally containing one or more O atoms, where the $C_{1-20}$ straight or branched alkyl chain optionally containing one or more O atoms is unsubstituted or substituted.

In still further embodiments, W is

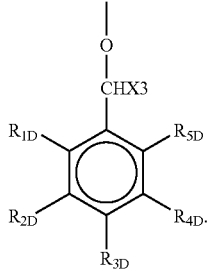

In certain embodiments, one of $R_{1D}$ or $R_{5D}$ is nitro with the other being selected from hydrogen, $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, arylcarbonylmethylene group, cyano, or hydroxyl, the $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, and arylcarbonylmethylene group being unsubstituted or substituted and either of $R_{2D}$, $R_{3D}$, or $R_{4D}$ is Z or hydrogen. In other embodiments, both of $R_{1D}$ and $R_{5D}$ are nitro.

In other embodiments, $R_{3D}$ is Z and either each of $R_{1D}$, $R_{2D}$, and $R_{4D}$ are independently hydrogen or $C_{1-20}$ straight or branched alkyl chain optionally containing one or more O atoms and $R_{5D}$ is nitro;

each of $R_{2D}$, $R_{4D}$, and $R_{5D}$ are independently hydrogen or $C_{1-20}$ straight or branched alkyl chain optionally containing one or more O atoms and $R_{1D}$ is nitro; or each of $R_{2D}$, and $R_{4D}$ are independently hydrogen or $C_{1-20}$ straight or branched alkyl chain optionally containing one or more O atoms and $R_{1D}$ and $R_{5D}$ are nitro, where the $C_{1-20}$ straight or branched alkyl chain optionally containing one or more O atoms is unsubstituted or substituted.

In yet other embodiments, Ar is either naphthyl or anthryl, each of which can be unsubstituted or substituted, and Y and W and the respective substituents are as described above.

Examples of $A^-$, the anion, include those commonly found with photoacid generators and can include, for example, $CF_3SO_3^-$, $CHF_2SO_3^-$, $CH_3SO_3^-$, $CCl_3SO_3^-$, $C_2F_5SO_3^-$, $C_2HF_4SO_3^-$, $C_4F_9SO_3^-$, pentafluorobenzene sulfonate, $(R_fSO_2)_3C^-$ and $(R_fSO_2)_2N^-$, wherein each $R_f$ is independently selected from the group consisting of highly fluorinated or perfluorinated alkyl or fluorinated aryl radicals and may be cyclic, when a combination of any two $R_f$ groups are linked to form a bridge, further, the $R_f$ alkyl chains contain from 1-20 carbon atoms and may be straight, branched, or cyclic, such that divalent oxygen, trivalent nitrogen or hexavalent sulfur may interrupt the skeletal chain, further when $R_f$ contains a cyclic structure, such structure has 5 or 6 ring members, optionally, 1 or 2 of which are heteroatoms. Examples include $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(CF_3SO_2)(C_4F_9SO_2)N^-$, $(C_2F_5SO_2)_3C^-$, $(C_4F_9SO_2)_3C^-$, $(CF_3SO_2)_2(C_2F_5SO_2)C^-$, $(C_4F_9SO_2)(C_2F_5SO_2)_2C^-$, $(CF_3SO_2)(C_4F_9SO_2)N^-$, $[(CF_3)_2NC_2F_4SO_2]_2N^-$, $(CF_3)_2NC_2F_4SO_2C^-(SO_2CF_3)_2$, $(3,5\text{-bis}(CF_3)C_6H_3)SO_2N^-SO_2CF_3$, $C_6F_5SO_2C^-(SO_2CF_3)_2$, $C_6F_5SO_2N^{31}\ SO_2CF_3$,

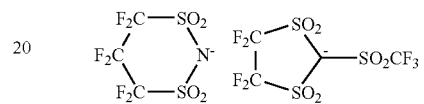

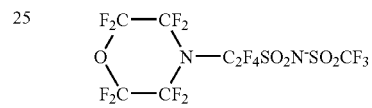

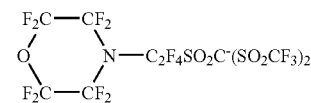

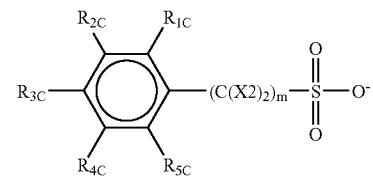

where $R_{1C}$, $R_{2C}$, $R_{3C}$, $R_{4C}$, $R_{5C}$, X2, and m are as disclosed above.

The present invention also relates to photoresist compositions useful for imaging in deep UV comprising a) a polymer containing an acid labile group, and, b) a compound of the present invention, which optionally contains another photoactive compound.

The invention also relates to a process for imaging a photoresist comprising the steps of a) coating a substrate with the novel photoresist composition, b) baking the substrate to substantially remove the solvent, c) image-wise exposing the photoresist coating, d) post-exposure baking the photoresist coating, and e) developing the photoresist coating with an aqueous alkaline solution.

DETAILED DESCRIPTION OF THE INVENTION

The present invention relates to a compound of the formula

Y—Ar where Ar is selected from

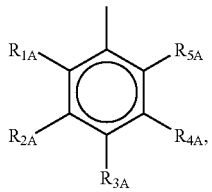

naphthyl, or anthryl;

Y is selected from

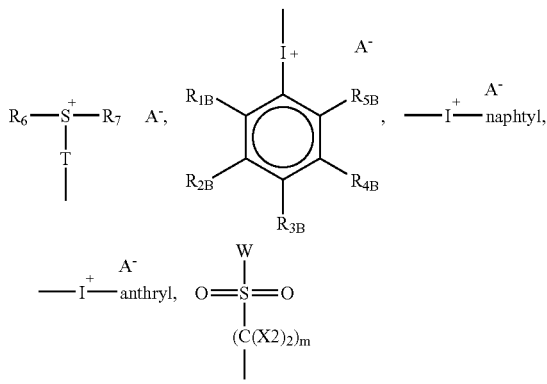

where W is selected from

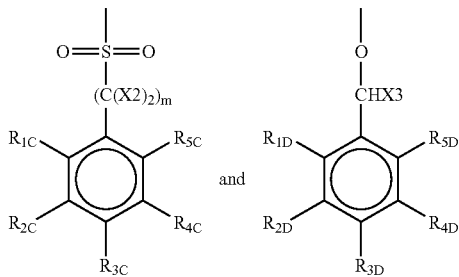

$R_{1A}$, $R_{1B}$, $R_{1C}$, $R_{2A}$, $R_{2B}$, $R_{2C}$, $R_{2D}$, $R_{3A}$, $R_{3B}$, $R_{3C}$, $R_{3D}$, $R_{4A}$, $R_{4B}$, $R_{4C}$, $R_{4D}$, $R_{5A}$, $R_{5B}$ and $R_{5C}$, are each independently selected from Z, hydrogen, $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, arylcarbonylmethylene group, $C_{1-20}$ straight or branched alkoxy chain, nitro, cyano, tresyl, or hydroxyl; either (i) one of $R_{1D}$ or $R_{5D}$ is nitro with the other being selected from hydrogen, $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, arylcarbonylmethylene group, cyano, or hydroxyl or (ii) both of $R_{1D}$ and $R_{5D}$ are nitro; $R_6$ and $R_7$ are each independently selected from $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, arylcarbonylmethylene group, nitro, cyano, or hydroxyl or $R_6$ and $R_7$ together with the S atom to which they are attached form a 5-, 6-, or 7-membered saturated or unsaturated ring optionally containing one or more O atoms which can be unsubstituted or substituted; T is a direct bond, a divalent $C_{1-20}$ straight or branched alkyl group optionally containing one or more O atoms, divalent $C_{5-50}$ aryl group, divalent $C_{5-50}$ aralkyl group, or divalent $C_{5-50}$ monocyclic, bicyclic or tricyclic alkyl group; Z is —(V)$_j$—(C(X11)(X12))$_n$—O—C(=O)—R$_8$, where either (i) one of X11 or X12 is $C_{1-20}$ straight or branched alkyl chain containing at least one fluorine atom and the other is hydrogen, halogen, or $C_{1-20}$ straight or branched alkyl chain or (ii) both of X11 and X12 are $C_{1-20}$ straight or branched alkyl chain containing at least one fluorine atom; V is a linkage group selected from a direct bond, a divalent $C_{1-20}$ straight or branched alkyl group optionally containing one or more O atoms, divalent $C_{5-50}$ aryl group, divalent $C_{5-50}$ aralkyl group, or divalent $C_{5-50}$ monocyclic, bicyclic or tricyclic alkyl group; X2 is hydrogen, halogen, or $C_{1-20}$ straight or branched alkyl chain optionally containing one or more O atoms; $R_8$ is a $C_{1-20}$ straight or branched alkyl chain optionally containing one or more O atoms, a $C_{5-50}$ monocyclic, bicyclic, or tricyclic alkyl group, or a $C_{5-50}$ aryl group; X3 is hydrogen, $C_{1-20}$ straight or branched alkyl chain, halogen, cyano, or —C(=O)—R$_{50}$ where R$_{50}$ is selected from $C_{1-20}$ straight or branched alkyl chain optionally containing one or more O atoms or —O—R$_{51}$ where R$_{51}$ is hydrogen or $C_{1-20}$ straight or branched alkyl chain; j is 0 to 10; m is 0 to 10; and n is 0 to 10, the $C_{1-20}$ straight or branched alkyl chain optionally containing one or more O atoms, $C_{1-20}$ straight or branched alkyl chain, $C_{1-20}$ straight or branched alkoxy chain, $C_{5-50}$ monocyclic, bicyclic, or tricyclic alkyl group, $C_{5-50}$ cyclic alkylcarbonyl group, $C_{5-50}$ aralkyl group, $C_{5-50}$ aryl group, naphthyl, anthryl, 5-, 6-, or 7-membered saturated or unsaturated ring optionally containing one or more O atoms, or arylcarbonylmethylene group being unsubstituted or substituted by one or more groups selected from the group consisting of Z, halogen, $C_{1-20}$ alkyl, $C_{3-20}$ cyclic alkyl, $C_{1-20}$ alkoxy, $C_{3-20}$ cyclic alkoxy, di $C_{1-20}$ alkylamino, dicyclic di $C_{1-20}$ alkylamino, hydroxyl, cyano, nitro, tresyl, oxo, aryl, aralkyl, oxygen atom, $CF_3SO_3$, aryloxy, arylthio, and groups of formulae (II) to (VI):

(II)

(III)

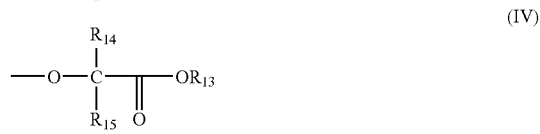

(IV)

(V)

-continued

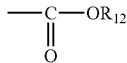
(VI)

$R_{10}$ and $R_{11}$ each independently represent a hydrogen atom, a $C_{1-20}$ straight or branched alkyl chain optionally containing one or more O atoms, or a $C_{5-50}$ monocyclic, bicyclic, or tricyclic alkyl group, or $R_{10}$ and $R_{11}$ together can represent an alkylene group to form a five- or six-membered ring, $R_{12}$ represents a $C_{1-20}$ straight or branched alkyl chain optionally containing one or more O atoms, a $C_{5-50}$ monocyclic, bicyclic, or tricyclic alkyl group, or a $C_{5-50}$ aralkyl group, or $R_{10}$ and $R_{12}$ together represent an alkylene group which forms a five- or six-membered ring together with the interposing —C—O— group, the carbon atom in the ring being optionally substituted by an oxygen atom, $R_{13}$ represents a $C_{1-20}$ straight or branched alkyl chain optionally containing one or more O atoms or a $C_{5-50}$ monocyclic, bicyclic, or tricyclic alkyl group, $R_{14}$ and $R_{15}$ each independently represent a hydrogen atom, a $C_{1-20}$ straight or branched alkyl chain optionally containing one or more O atoms or a $C_{5-50}$ monocyclic, bicyclic, or tricyclic alkyl group, $R_{16}$ represents a $C_{1-20}$ straight or branched alkyl chain optionally containing one or more O atoms, a $C_{5-50}$ monocyclic, bicyclic, or tricyclic alkyl group, a $C_{5-50}$ aryl group, or a $C_{5-50}$ aralkyl group, and $R_{17}$ represents $C_{1-20}$ straight or branched alkyl chain optionally containing one or more O atoms, a $C_{5-50}$ monocyclic, bicyclic, or tricyclic alkyl group, a $C_{5-50}$ aryl group, a $C_{5-50}$ aralkyl group, the group —Si(R$_{16}$)$_2$R$_{17}$, or the group —O—Si(R$_{16}$)$_2$R$_{17}$, the $C_{1-20}$ straight or branched alkyl chain optionally containing one or more O atoms, $C_{5-50}$ monocyclic, bicyclic, or tricyclic alkyl group, $C_{5-50}$ aryl group, and $C_{5-50}$ aralkyl group being unsubstituted or substituted as above; and $A^-$ is an anion.

In certain embodiments, Ar is

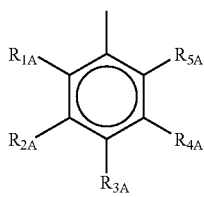

and Y is

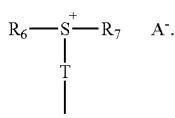

In other embodiments, $R_6$ and $R_7$ are each independently selected from $C_{1-20}$ straight or branched alkyl chain optionally containing one or more O atoms or $C_{5-50}$ aryl group and each of $R_{1A}$, $R_{2A}$, $R_{3A}$, $R_{4A}$, and $R_{5A}$ are independently selected from Z, hydrogen, or $C_{1-20}$ straight or branched alkyl chain optionally containing one or more O atoms, the $C_{1-20}$ straight or branched alkyl chain optionally containing one or more O atoms or $C_{5-50}$ aryl group being unsubstituted or substituted.

In further embodiments, either one of $R_{1A}$, $R_{2A}$, $R_{3A}$, $R_{4A}$, or $R_{5A}$ is Z.

In further embodiments, $R_6$ and $R_7$ are each independently $C_{1-20}$ straight or branched alkyl chain optionally containing one or more O atoms, $R_{3A}$ is Z and either each of $R_{1A}$, $R_{2A}$, $R_{4A}$, and $R_{5A}$ are hydrogen;

each of $R_{1A}$, $R_{2A}$, and $R_{4A}$ are hydrogen and $R_{5A}$ is $C_{1-20}$ straight or branched alkyl chain optionally containing one or more O atoms;

each of $R_{1A}$, $R_{2A}$, and $R_{5A}$ are hydrogen and $R_{4A}$ is $C_{1-20}$ straight or branched alkyl chain optionally containing one or more O atoms;

each of $R_{1A}$, $R_{4A}$, and $R_{5A}$ are hydrogen and $R_{2A}$ is $C_{1-20}$ straight or branched alkyl chain optionally containing one or more O atoms;

each of $R_{2A}$, $R_{4A}$, and $R_{5A}$ are hydrogen and $R_{1A}$ is $C_{1-20}$ straight or branched alkyl chain optionally containing one or more O atoms;

each of $R_{4A}$ and $R_{5A}$ are hydrogen and $R_{1A}$ and $R_{2A}$ are $C_{1-20}$ straight or branched alkyl chain optionally containing one or more O atoms;

each of $R_{2A}$ and $R_{5A}$ are hydrogen and $R_{1A}$ and $R_{4A}$ are $C_{1-20}$ straight or branched alkyl chain optionally containing one or more O atoms;

each of $R_{2A}$ and $R_{4A}$ are hydrogen and $R_{1A}$ and $R_{5A}$ are $C_{1-20}$ straight or branched alkyl chain optionally containing one or more O atoms;

each of $R_{1A}$ and $R_{5A}$ are hydrogen and $R_{2A}$ and $R_{4A}$ are $C_{1-20}$ straight or branched alkyl chain optionally containing one or more O atoms;

each of $R_{1A}$ and $R_{4A}$ are hydrogen and $R_{2A}$ and $R_{5A}$ are $C_{1-20}$ straight or branched alkyl chain optionally containing one or more O atoms;

each of $R_{1A}$ and $R_{2A}$ are hydrogen and $R_{4A}$ and $R_{5A}$ are $C_{1-20}$ straight or branched alkyl chain optionally containing one or more O atoms;

$R_{5A}$ is hydrogen and $R_{1A}$, $R_{2A}$ and $R_{4A}$ are $C_{1-20}$ straight or branched alkyl chain optionally containing one or more O atoms;

$R_{4A}$ is hydrogen and $R_{1A}$, $R_{2A}$ and $R_{5A}$ are $C_{1-20}$ straight or branched alkyl chain optionally containing one or more O atoms;

$R_{2A}$ is hydrogen and $R_{1A}$, $R_{4A}$ and $R_{5A}$ are $C_{1-20}$ straight or branched alkyl chain optionally containing one or more O atoms;

$R_{1A}$ is hydrogen and $R_{2A}$, $R_{4A}$ and $R_{5A}$ are $C_{1-20}$ straight or branched alkyl chain optionally containing one or more O atoms; or each of $R_{1A}$, $R_{2A}$, $R_{4A}$, and $R_{5A}$ are $C_{1-20}$ straight or branched alkyl chain optionally containing one or more O atoms, where the $C_{1-20}$ straight or branched alkyl chain optionally containing one or more O atoms is unsubstituted or substituted.

In further embodiments, $R_6$ and $R_7$ are each independently $C_{5-50}$ aryl group, $R_{3A}$ is Z and either each of $R_{1A}$, $R_{2A}$, $R_{4A}$, and $R_{5A}$ are hydrogen;

each of $R_{1A}$, $R_{2A}$, and $R_{4A}$ are hydrogen and $R_{5A}$ is $C_{1-20}$ straight or branched alkyl chain optionally containing one or more O atoms;

each of $R_{1A}$, $R_{2A}$, and $R_{5A}$ are hydrogen and $R_{4A}$ is $C_{1-20}$ straight or branched alkyl chain optionally containing one or more O atoms;

each of $R_{1A}$, $R_{4A}$, and $R_{5A}$ are hydrogen and $R_{2A}$ is $C_{1-20}$ straight or branched alkyl chain optionally containing one or more O atoms;

each of $R_{2A}$, $R_{4A}$, and $R_{5A}$ are hydrogen and $R_{1A}$ is $C_{1-20}$ straight or branched alkyl chain optionally containing one or more O atoms;

each of $R_{4A}$ and $R_{5A}$ are hydrogen and $R_{1A}$ and $R_{2A}$ are $C_{1-20}$ straight or branched alkyl chain optionally containing one or more O atoms;

each of $R_{2A}$ and $R_{5A}$ are hydrogen and $R_{1A}$ and $R_{4A}$ are $C_{1-20}$ straight or branched alkyl chain optionally containing one or more O atoms;

each of $R_{2A}$ and $R_{4A}$ are hydrogen and $R_{1A}$ and $R_{5A}$ are $C_{1-20}$ straight or branched alkyl chain optionally containing one or more O atoms;

each of $R_{1A}$ and $R_{5A}$ are hydrogen and $R_{2A}$ and $R_{4A}$ are $C_{1-20}$ straight or branched alkyl chain optionally containing one or more O atoms;

each of $R_{1A}$ and $R_{4A}$ are hydrogen and $R_{2A}$ and $R_{5A}$ are $C_{1-20}$ straight or branched alkyl chain optionally containing one or more O atoms;

each of $R_{1A}$ and $R_{2A}$ are hydrogen and $R_{4A}$ and $R_{5A}$ are $C_{1-20}$ straight or branched alkyl chain optionally containing one or more O atoms;

$R_{5A}$ is hydrogen and $R_{1A}$, $R_{2A}$ and $R_{4A}$ are $C_{1-20}$ straight or branched alkyl chain optionally containing one or more O atoms;

$R_{4A}$ is hydrogen and $R_{1A}$, $R_{2A}$ and $R_{5A}$ are $C_{1-20}$ straight or branched alkyl chain optionally containing one or more O atoms;

$R_{2A}$ is hydrogen and $R_{1A}$, $R_{4A}$ and $R_{5A}$ are $C_{1-20}$ straight or branched alkyl chain optionally containing one or more O atoms;

$R_{1A}$ is hydrogen and $R_{2A}$, $R_{4A}$ and $R_{5A}$ are $C_{1-20}$ straight or branched alkyl chain optionally containing one or more O atoms; or each of $R_{1A}$, $R_{2A}$, $R_{4A}$, and $R_{5A}$ are $C_{1-20}$ straight or branched alkyl chain optionally containing one or more O atoms, where the $C_{1-20}$ straight or branched alkyl chain optionally containing one or more O atoms is unsubstituted or substituted.

In other embodiments, Ar is

[structure: benzene ring with substituents $R_{1A}$, $R_{2A}$, $R_{3A}$, $R_{4A}$, $R_{5A}$]

and Y is

[structure: iodonium benzene ring with $I^+$ $A^-$ and substituents $R_{1B}$, $R_{2B}$, $R_{3B}$, $R_{4B}$, $R_{5B}$]

In further embodiments, either one of $R_{1B}$, $R_{2B}$, $R_{3B}$, $R_{4B}$, or $R_{5B}$ is Z or hydrogen.

In further embodiments, $R_{3A}$ is Z and either each of $R_{1A}$, $R_{2A}$, $R_{4A}$, and $R_{5A}$ are hydrogen;

each of $R_{1A}$, $R_{2A}$, and $R_{4A}$ are hydrogen and $R_{5A}$ is $C_{1-20}$ straight or branched alkyl chain optionally containing one or more O atoms;

each of $R_{1A}$, $R_{2A}$, and $R_{5A}$ are hydrogen and $R_{4A}$ is $C_{1-20}$ straight or branched alkyl chain optionally containing one or more O atoms;

each of $R_{1A}$, $R_{4A}$, and $R_{5A}$ are hydrogen and $R_{2A}$ is $C_{1-20}$ straight or branched alkyl chain optionally containing one or more O atoms;

each of $R_{2A}$, $R_{4A}$, and $R_{5A}$ are hydrogen and $R_{1A}$ is $C_{1-20}$ straight or branched alkyl chain optionally containing one or more O atoms;

each of $R_{4A}$ and $R_{5A}$ are hydrogen and $R_{1A}$ and $R_{2A}$ are $C_{1-20}$ straight or branched alkyl chain optionally containing one or more O atoms;

each of $R_{2A}$ and $R_{5A}$ are hydrogen and $R_{1A}$ and $R_{4A}$ are $C_{1-20}$ straight or branched alkyl chain optionally containing one or more O atoms;

each of $R_{2A}$ and $R_{4A}$ are hydrogen and $R_{1A}$ and $R_{5A}$ are $C_{1-20}$ straight or branched alkyl chain optionally containing one or more O atoms;

each of $R_{1A}$ and $R_{5A}$ are hydrogen and $R_{2A}$ and $R_{4A}$ are $C_{1-20}$ straight or branched alkyl chain optionally containing one or more O atoms;

each of $R_{1A}$ and $R_{4A}$ are hydrogen and $R_{2A}$ and $R_{5A}$ are $C_{1-20}$ straight or branched alkyl chain optionally containing one or more O atoms;

each of $R_{1A}$ and $R_{2A}$ are hydrogen and $R_{4A}$ and $R_{5A}$ are $C_{1-20}$ straight or branched alkyl chain optionally containing one or more O atoms;

$R_{5A}$ is hydrogen and $R_{1A}$, $R_{2A}$ and $R_{4A}$ are $C_{1-20}$ straight or branched alkyl chain optionally containing one or more O atoms;

$R_{4A}$ is hydrogen and $R_{1A}$, $R_{2A}$ and $R_{5A}$ are $C_{1-20}$ straight or branched alkyl chain optionally containing one or more O atoms;

$R_{2A}$ is hydrogen and $R_{1A}$, $R_{4A}$ and $R_{5A}$ are $C_{1-20}$ straight or branched alkyl chain optionally containing one or more O atoms;

$R_{1A}$ is hydrogen and $R_{2A}$, $R_{4A}$ and $R_{5A}$ are $C_{1-20}$ straight or branched alkyl chain optionally containing one or more O atoms; or each of $R_{1A}$, $R_{2A}$, $R_{4A}$, and $R_{5A}$ are $C_{1-20}$ straight or branched alkyl chain optionally containing one or more O atoms, wherein the $C_{1-20}$ straight or branched alkyl chain optionally containing one or more O atoms is unsubstituted or substituted.

In further embodiments, $R_{3B}$ is Z or hydrogen and either
each of $R_{1B}$, $R_{2B}$, $R_{4B}$, and $R_{5B}$ are hydrogen;

each of $R_{1B}$, $R_{2B}$, and $R_{4B}$ are hydrogen and $R_{5B}$ is $C_{1-20}$ straight or branched alkyl chain optionally containing one or more O atoms;

each of $R_{1B}$, $R_{2B}$, and $R_{5B}$ are hydrogen and $R_{4B}$ is $C_{1-20}$ straight or branched alkyl chain optionally containing one or more O atoms;

each of $R_{1B}$, $R_{4B}$, and $R_{5B}$ are hydrogen and $R_{2B}$ is $C_{1-20}$ straight or branched alkyl chain optionally containing one or more O atoms;

each of $R_{2B}$, $R_{4B}$, and $R_{5B}$ are hydrogen and $R_{1B}$ is $C_{1-20}$ straight or branched alkyl chain optionally containing one or more O atoms;

each of $R_{4B}$ and $R_{5B}$ are hydrogen and $R_{1B}$ and $R_{2B}$ are $C_{1-20}$ straight or branched alkyl chain optionally containing one or more O atoms;

each of $R_{2B}$ and $R_{5B}$ are hydrogen and $R_{1B}$ and $R_{4B}$ are $C_{1-20}$ straight or branched alkyl chain optionally containing one or more O atoms;

each of $R_{2B}$ and $R_{4B}$ are hydrogen and $R_{1B}$ and $R_{5B}$ are $C_{1-20}$ straight or branched alkyl chain optionally containing one or more O atoms;

each of $R_{1B}$ and $R_{5B}$ are hydrogen and $R_{2B}$ and $R_{4B}$ are $C_{1-20}$ straight or branched alkyl chain optionally containing one or more O atoms;

each of $R_{1B}$ and $R_{4B}$ are hydrogen and $R_{2B}$ and $R_{5B}$ are $C_{1-20}$ straight or branched alkyl chain optionally containing one or more O atoms;

each of $R_{1B}$ and $R_{2B}$ are hydrogen and $R_{4B}$ and $R_{5B}$ are $C_{1-20}$ straight or branched alkyl chain optionally containing one or more O atoms;

$R_{5B}$ is hydrogen and $R_{1B}$, $R_{2B}$ and $R_{4B}$ are $C_{1-20}$ straight or branched alkyl chain optionally containing one or more O atoms;

$R_{4B}$ is hydrogen and $R_{1B}$, $R_{2B}$ and $R_{5B}$ are $C_{1-20}$ straight or branched alkyl chain optionally containing one or more O atoms;

$R_{2B}$ is hydrogen and $R_{1B}$, $R_{4B}$ and $R_{5B}$ are $C_{1-20}$ straight or branched alkyl chain optionally containing one or more O atoms;

$R_{1B}$ is hydrogen and $R_{2B}$, $R_{4B}$ and $R_{5B}$ are $C_{1-20}$ straight or branched alkyl chain optionally containing one or more O atoms; or each of $R_{1B}$, $R_{2B}$, $R_{4B}$, and $R_{5B}$ are $C_{1-20}$ straight or branched alkyl chain optionally containing one or more O atoms, where the $C_{1-20}$ straight or branched alkyl chain optionally containing one or more O atoms is unsubstituted or substituted.

In other embodiments, Ar is

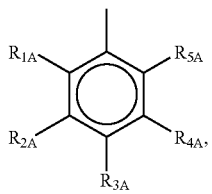

Y is

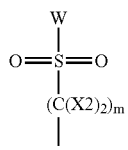

and W is

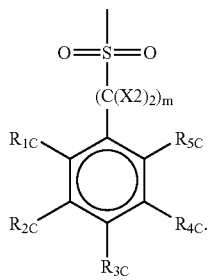

Further embodiments include those where $R_{3A}$ is Z and $R_{1A}$, $R_{2A}$, $R_{4A}$, and $R_{5A}$ are as described above. In further embodiments, X2 is selected from hydrogen, methyl or perfluoromethyl and m is 1. In further embodiments, $R_{3C}$ is Z or hydrogen with either each of $R_{1C}$, $R_{4C}$, and $R_{5C}$ are hydrogen and $R_{2C}$ is $C_{1-20}$ straight or branched alkyl chain optionally containing one or more O atoms;

each of $R_{2C}$, $R_{4C}$, and $R_{5C}$ are hydrogen and $R_{1C}$ is $C_{1-20}$ straight or branched alkyl chain optionally containing one or more O atoms;

each of $R_{4C}$ and $R_{5C}$ are hydrogen and $R_{1C}$ and $R_{2C}$ are $C_{1-20}$ straight or branched alkyl chain optionally containing one or more O atoms;

each of $R_{2C}$ and $R_{5C}$ are hydrogen and $R_{1C}$ and $R_{4C}$ are $C_{1-20}$ straight or branched alkyl chain optionally containing one or more O atoms;

each of $R_{2C}$ and $R_{4C}$ are hydrogen and $R_{1C}$ and $R_{5C}$ are $C_{1-20}$ straight or branched alkyl chain optionally containing one or more O atoms;

each of $R_{1C}$ and $R_{5C}$ are hydrogen and $R_{2C}$ and $R_{4C}$ are $C_{1-20}$ straight or branched alkyl chain optionally containing one or more O atoms;

each of $R_{1C}$ and $R_{4C}$ are hydrogen and $R_{2C}$ and $R_{5C}$ are $C_{1-20}$ straight or branched alkyl chain optionally containing one or more O atoms;

each of $R_{1C}$ and $R_{2C}$ are hydrogen and $R_{4C}$ and $R_{5C}$ are $C_{1-20}$ straight or branched alkyl chain optionally containing one or more O atoms;

$R_{5C}$ is hydrogen and $R_{1C}$, $R_{2C}$ and $R_{4C}$ are $C_{1-20}$ straight or branched alkyl chain optionally containing one or more O atoms;

$R_{4C}$ is hydrogen and $R_{1C}$, $R_{2C}$ and $R_{5C}$ are $C_{1-20}$ straight or branched alkyl chain optionally containing one or more O atoms;

$R_{2C}$ is hydrogen and $R_{1C}$, $R_{4C}$ and $R_{5C}$ are $C_{1-20}$ straight or branched alkyl chain optionally containing one or more O atoms;

$R_{1C}$ is hydrogen and $R_{2C}$, $R_{4C}$ and $R_{5C}$ are $C_{1-20}$ straight or branched alkyl chain optionally containing one or more O atoms; or each of $R_{1C}$, $R_{2C}$, $R_{4C}$, and $R_{5C}$ are $C_{1-20}$ straight or branched alkyl chain optionally containing one or more O atoms, where the $C_{1-20}$ straight or branched alkyl chain optionally containing one or more O atoms is unsubstituted or substituted.

In still further embodiments, W is

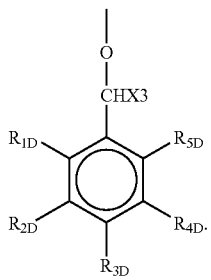

In certain embodiments, one of $R_{1D}$ or $R_{5D}$ is nitro with the other being selected from hydrogen, $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, arylcarbonylmethylene group, cyano, or hydroxyl, the $C_{1-20}$ straight or branched alkyl chain optionally containing one or more O atoms, $C_{5-50}$ monocyclic, bicyclic, or tricyclic alkyl group, $C_{5-50}$ cyclic alkylcarbonyl group, $C_{5-50}$ aryl group, $C_{5-50}$ aralkyl group, and arylcarbonylmethylene group being unsubstituted or substituted and either of $R_{2D}$, $R_{3D}$, or $R_{4D}$ is Z or hydrogen. In other embodiments, both of $R_{1D}$ and $R_{5D}$ are nitro.

In other embodiments, $R_{3D}$ is Z and either each of $R_{1D}$, $R_{2D}$, and $R_{4D}$ are independently hydrogen or $C_{1-20}$ straight or branched alkyl chain optionally containing one or more O atoms and $R_{5D}$ is nitro;

each of $R_{2D}$, $R_{4D}$, and $R_{5D}$ are independently hydrogen or $C_{1-20}$ straight or branched alkyl chain optionally containing one or more O atoms and $R_{1D}$ is nitro; or each of $R_{2D}$, and $R_{4D}$ are independently hydrogen or $C_{1-20}$ straight or branched alkyl chain optionally containing one or more O atoms and $R_{1D}$ and $R_{5D}$ are nitro, where the $C_{1-20}$ straight or branched alkyl chain optionally containing one or more O atoms is unsubstituted or substituted.

In yet other embodiments, Ar is either naphthyl or anthryl, each of which can be unsubstituted or substituted, and Y and W and the respective substituents are as described above.

Non-limiting examples of the compounds of the present invention include, for example, (A)

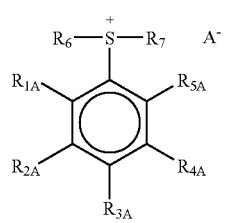

(B)

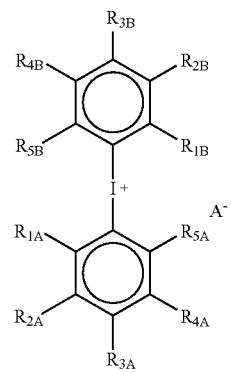

(C)

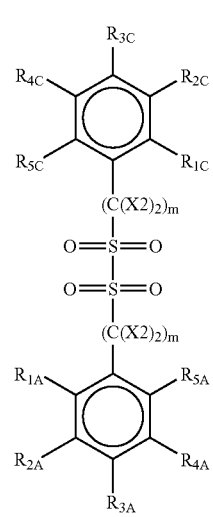

(D)

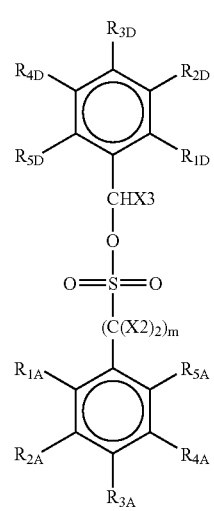

-continued
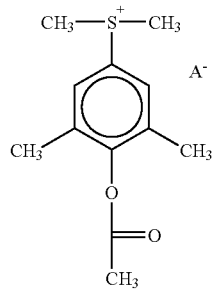
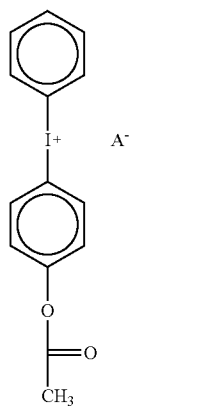
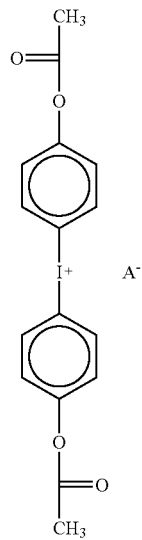
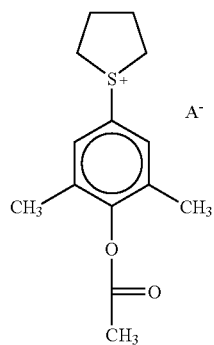
-continued
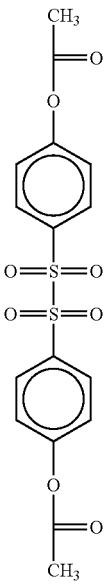
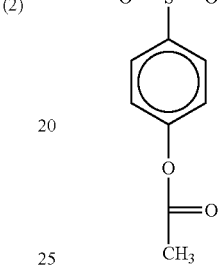
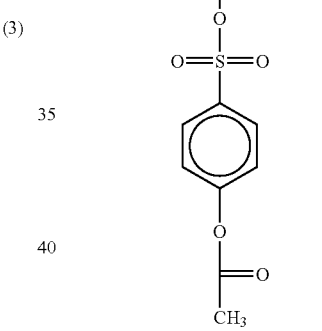
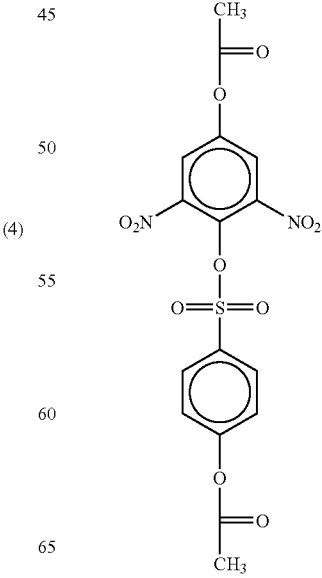

-continued

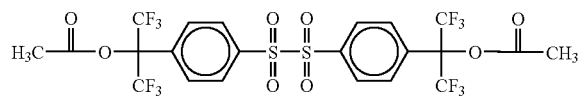
(8)

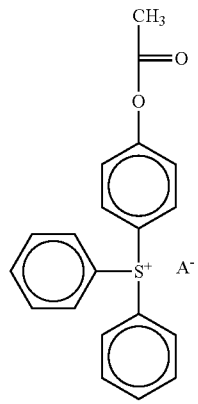
(9)

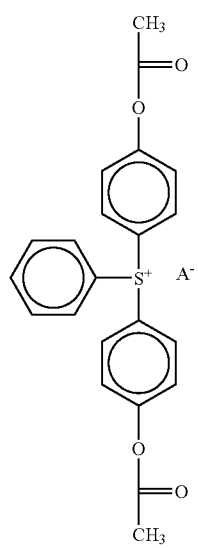
(10)

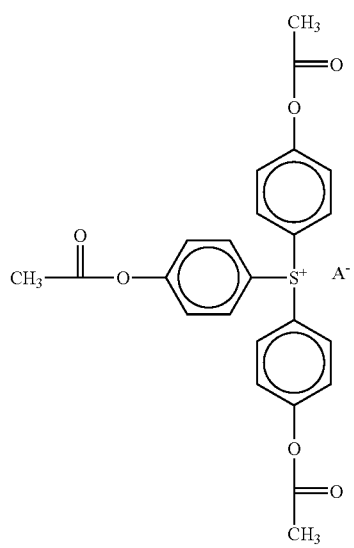
(11)

where examples of A⁻, the anion, include those commonly found with photoacid generators and can include, for example, $CF_3SO_3^-$, $CHF_2SO_3^-$, $CH_3SO_3^-$, $CCl_3SO_3^-$, $C_2F_5SO_3^-$, $C_2HF_4SO_3^-$, $C_4F_9SO_3^-$, pentafluorobenzene sulfonate, $(R_fSO_2)_3C^-$ and $(R_fSO_2)_2N^-$, wherein each $R_f$ is independently selected from the group consisting of highly fluorinated or perfluorinated alkyl or fluorinated aryl radicals and may be cyclic, when a combination of any two $R_f$ groups are linked to form a bridge, further, the $R_f$ alkyl chains contain from 1-20 carbon atoms and may be straight, branched, or cyclic, such that divalent oxygen, trivalent nitrogen or hexavalent sulfur may interrupt the skeletal chain, further when $R_f$ contains a cyclic structure, such structure has 5 or 6 ring members, optionally, 1 or 2 of which are heteroatoms. Examples include $(C_2F_5SO_2)_2N^-$, $(C_4F_9SO_2)_2N^-$, $(C_8F_{17}SO_2)_3C^-$, $(CF_3SO_2)_3C^-$, $(CF_3SO_2)_2N^-$, $(CF_3SO_2)(C_4F_9SO_2)N^-$, $(C_2F_5SO_2)_3C^-$, $(C_4F_9SO_2)_3C^-$, $(CF_3SO_2)_2(C_2F_5SO_2)C^-$, $(C_4F_9SO_2)(C_2F_5SO_2)_2C^-$, $(CF_3SO_2)(C_4F_9SO_2)N^-$, $[(CF_3)_2NC_2F_4SO_2]_2N^-$, $(CF_3)_2NC_2F_4SO_2C^-(SO_2CF_3)_2$, $(3,5\text{-bis}(CF_3)C_6H_3)SO_2N^-SO_2CF_3$, $C_6F_5SO_2C^-(SO_2CF_3)_2$, $C_6F_5SO_2N^-SO_2CF_3$,

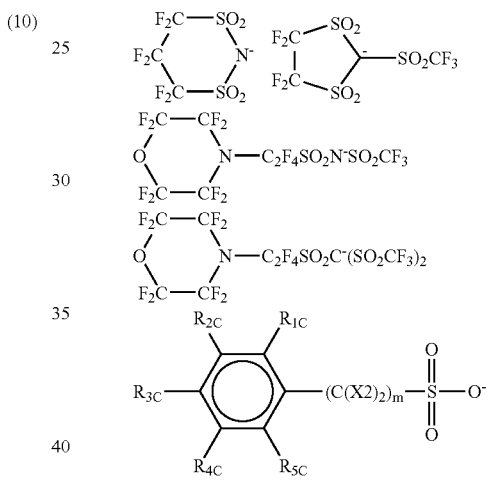

where $R_{1C}$, $R_{2C}$, $R_{3C}$, $R_{4C}$, $R_{5C}$, X2, and m are as disclosed above. The preparation of the various anions are disclosed in, for example, U.S. Pat. No. 5,554,664.

The use of dinitro benzene (for example, formulas (5) and (6) above) in photoactive compounds is described in U.S. Pat. Nos. 4,996,136 and 5,200,544, the contents of which are hereby incorporated herein by reference.

The present invention also relates to photoresist compositions useful for imaging in deep UV comprising a) a polymer containing an acid labile group, and, b) a compound of the present invention, which optionally contains another photoactive compound.

The invention also relates to a process for imaging a photoresist comprising the steps of a) coating a substrate with the novel photoresist composition, b) baking the substrate to substantially remove the solvent, c) image-wise exposing the photoresist coating, d) post-exposure baking the photoresist coating, and e) developing the photoresist coating with an aqueous alkaline solution.

The present invention is also related to other photoacid generators which contain the —(V)hd j—(C(X11)(X12))— O—C(=O)—$R_8$ group. For example, the —(V)—(C(X11) (X12))$_n$—O—C(=O)—$R_8$ group can be placed on photoacid generators such as:

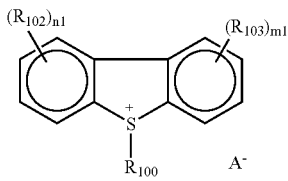

wherein $R_{100}$ is a $C_{1-20}$ straight or branched alkyl chain, $C_{5-50}$ monocyclic, bicyclic, or tricyclic alkyl group, $C_{5-50}$ cyclic alkylcarbonyl group, $C_{5-50}$ aryl group, or $C_{5-50}$ aralkyl group, the $C_{1-20}$ straight or branched alkyl chain, $C_{5-50}$ monocyclic, bicyclic, or tricyclic alkyl group, $C_{5-50}$ cyclic alkylcarbonyl group, $C_{5-50}$ aryl group, or $C_{5-50}$ aralkyl group being unsubstituted or substituted by one or more groups selected from halogen, $C_{1-20}$ straight or branched alkyl chain, $C_{1-8}$ perfluoroalkyl, $C_{1-20}$ alkoxy, cyano, hydroxyl, or nitro; $R_{102}$ and $R_{103}$ are each independently selected from hydrogen, $-(V)_j-(C(X11)(X12))_n-O-C(=O)-R_8$, nitro, cyano, or $C_{1-20}$ straight or branched alkyl chain optionally containing one or more O atoms, where $R_8$ is as described herein, $C_{1-20}$ straight or branched alkyl chain, $C_{1-20}$ alkoxy, nitro, halogen, carboxyl, hydroxyl, and sulfate; each of m1 and n1 are independently 0 or a positive integer; and A⁻ is an anion;

N-hydroxyimide sulfonic acid esters such as

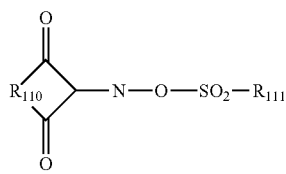

where $R_{110}$ is an arylene group of 6 to 10 carbon atoms, alkylene group of 1 to 6 carbon atoms, or alkenylene group of 2 to 6 carbon atoms, wherein at least a hydrogen atom of $R_{110}$ is replaced by $-(V)_j-(C(X11)(X12))_n-O-C(=O)-R_8$ and $R_{111}$ is as $R_{1A}$ described above and for example,

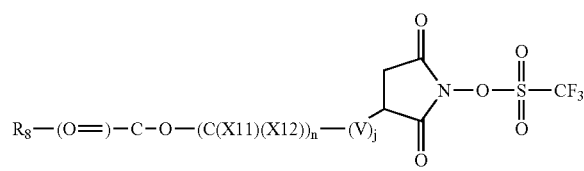

halogenated sulfonyloxy dicarboximides, for example those described in U.S. Pat. No. 6,406,828, which are substituted with a $-(V)_j-(C(X11)(X12))_n-O-C(=O)-R_8$ group; diazomethane derivatives; glyoxime deriviatives, bissulfone derivatives, β-ketosulfone derivatives, disulfone derivatives and the like wherein a hydrogen atom has been replaced by $V)_j-(C(X11)(X12))_n-O-C(=O)-R_8$.

Without wishing to be bound by theory, it is believed that the present inventive compounds, which contain carboxylate moieties, capping pendant phenol or fluoroalcohol moieties, will undergo base induced hydrolysis in an exposed region of the photoresist due to the hydrophilic nature of the surface which allows for fast cleavage of the carboxylate moiety. This, it is believed, prevents residual photoactive compound and/or photoproducts from hindering dissolution. It is also believed that the carboxylate capping groups allow the photoactive compound to maintain a good solubility in the resist casting solvent and matrix while at the same time providing for a mechanism to allow for base dissolution in the exposed area.

Polymers useful in the photoresist compositions include those that have acid labile groups that make the polymer insoluble in aqueous alkaline solution, but such a polymer in the presence of an acid catalytically deprotects the polymer, wherein the polymer then becomes soluble in an aqueous alkaline solution. The polymers preferably are transparent below 200 nm, and are essentially non-aromatic, and preferably are acrylates and/or cycloolefin polymers. Such polymers are, for example, but not limited to, those described in U.S. Pat. Nos. 5,843,624, 5,879,857, WO 97/33,198, EP 789,278 and GB 2,332,679. Nonaromatic polymers that are preferred for irradiation below 200 nm are substituted acrylates, cycloolefins, substituted polyethylenes, etc. Aromatic polymers based on polyhydroxystyrene and its copolymers may also be used, especially for 248 nm exposure.

Polymers based on acrylates are generally based on poly(meth)acrylates with at least one unit containing pendant alicyclic groups, and with the acid labile group being pendant from the polymer backbone and/or from the alicyclic group. Examples of pendant alicyclic groups, may be adamantyl, tricyclodecyl, isobornyl, menthyl and their derivatives. Other pendant groups may also be incorporated into the polymer, such as mevalonic lactone, gamma butyrolactone, alkyloxyalkyl, etc. Examples of structures for the alicyclic group include:

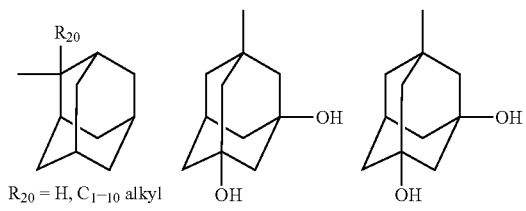

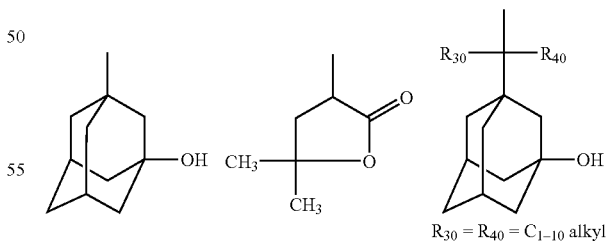

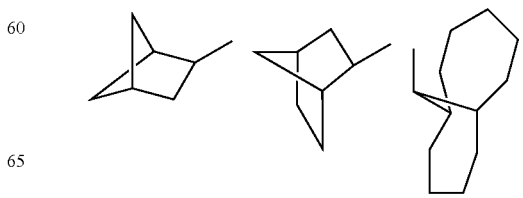

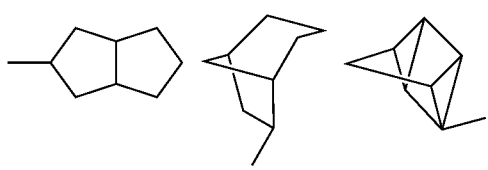
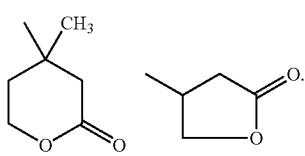
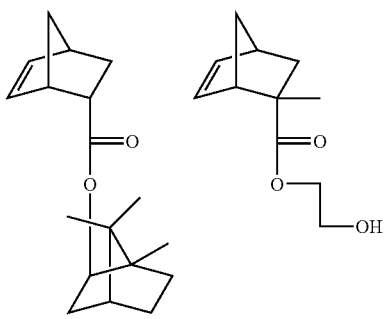

The type of monomers and their ratios incorporated into the polymer are optimized to give the best lithographic performance. Such polymers are described in R. R. Dammel et al., Advances in Resist Technology and Processing, SPIE, Vol. 3333, p 144, (1998). Examples of these polymers include poly(2-methyl-2-adamantane methacrylate-co-mevalonic lactone methacrylate), poly(carboxytetracyclododecyl methacrylate-co-tetrahydropyranylcarboxytetracyclododecyl methacrylate), poly(tricyclodecylacrylate-co-tetrahydropyranylmethacrylate-co-methacrylicacid), poly(3-oxocyclohexyl methacrylate-co-adamantyl-methacrylate).

Polymers synthesized from cycloolefins, with norbornene and tetracyclododecene derivatives, may be polymerized by ring-opening metathesis, free-radical polymerization or using metal organic catalysts. Cycloolefin derivatives may also be copolymerized with cyclic anhydrides or with maleimide or its derivatives. Examples of cyclic anhydrides are maleic anhydride and itaconic anhydride. The cycloolefin is incorporated into the backbone of the polymer and may be any substituted or unsubstituted multicyclic hydrocarbon containing an unsaturated bond. The monomer can have acid labile groups attached. The polymer may be synthesized from one or more cycloolefin monomers having an unsaturated bond. The cycloolefin monomers may be substituted or unsubstituted norbornene, or tetracyclododecane. The substituents on the cycloolefin may be aliphatic or cycloaliphatic alkyls, esters, acids, hydroxyl, nitrile or alkyl derivatives. Examples of cycloolefin monomers, without limitation, include:

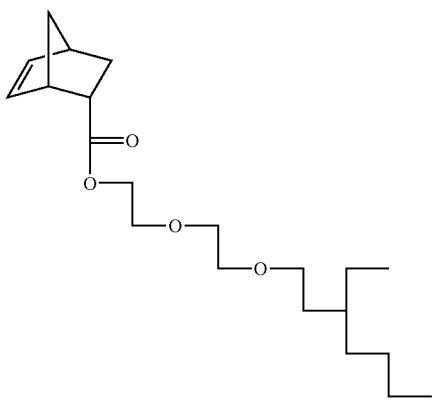
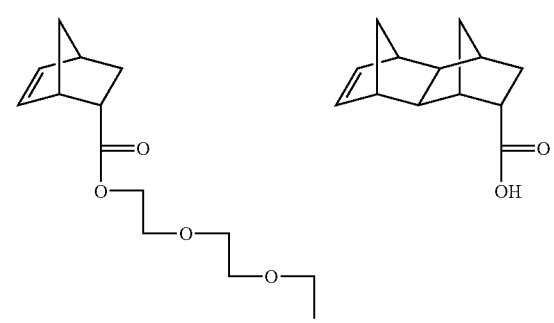
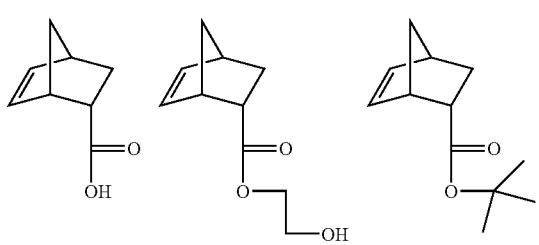
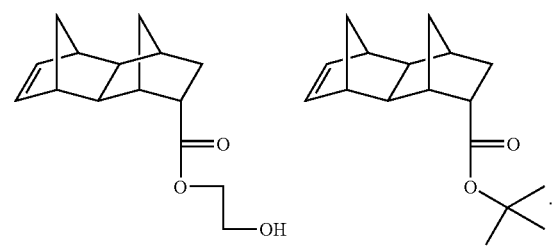

Other cycloolefin monomers which may also be used in synthesizing the polymer are:

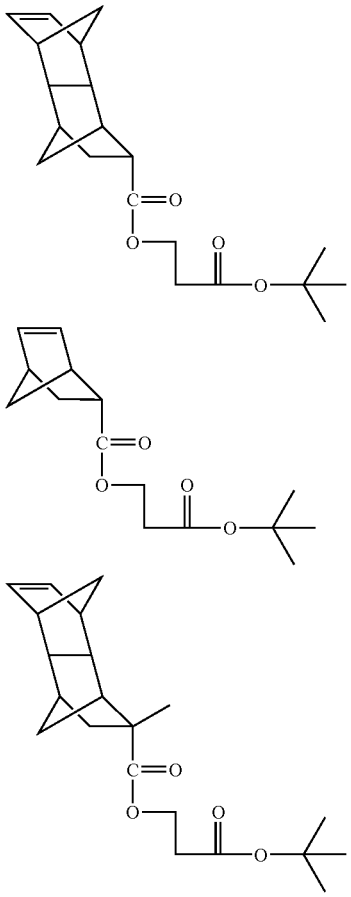

Such polymers are described in the following reference and incorporated herein, M-D. Rahman et al, Advances in Resist Technology and Processing, SPIE, Vol. 3678, p 1193, (1999). Examples of these polymers include poly((t-butyl 5-norbornene-2-carboxylate-co-2-hydroxyethyl 5-norbornene-2-carboxylate-co-5-norbornene-2-carboxylic acid-co-maleic anhydride), poly(t-butyl 5-norbornene-2-carboxylate-co-isobornyl-5-norbornene-2-carboxylate-co-2-hydroxyethyl 5-norbornene-2-carboxylate-co-5-norbornene-2-carboxylic acid-co-maleic anhydride), poly (tetracyclododecene-5-carboxylate-co-maleic anhydride), poly(t-butyl 5-norbornene-2-carboxylate-co-maleic anhydride-co-2-methyladamantyl methacrylate-co-2-mevalonic lactone methacrylate), poly(2-methyladamantyl methacrylate-co-2-mevalonic lactone methacylate) and the like.

Polymers containing mixtures of acrylate monomers, cycloolefinic monomers and cyclic anhydrides, where such monomers are described above, may also be combined into a hybrid polymer. Examples of cycloolefin monomers include those selected from t-butyl norbornene carboxylate (BNC), hydroxyethyl norbornene carboxylate (HNC), norbornene carboxylic acid (NC), t-butyltetracyclo[4.4.0.1.$^{2,}$ $_6$1.$^{7,10}$]dodec-8-ene-3-carboxylate, and t-butoxy carbonylmethyl tetracyclo[4.4.0.1.$^{2,6}$1.$^{7,10}$]dodec-8-ene-3-carboxylate. In some instances, preferred examples of cycloolefins include t-butyl norbornene carboxylate (BNC), hydroxyethyl norbornene carboxylate (HNC), and norbornene carboxylic acid (NC). Examples of acrylate monomers include those selected from mevaloniclactone methacrylate (MLMA), 2-methyladamantyl methacrylate (MAdMA), isoadamantyl methacrylate, 3-hydroxy-1-methacryloxyadamatane, 3,5-dihydroxy-1-methacryloxyadamantane, β-methacryloxy-γ-butyrolactone, γ-butyrolactone methacrylate (GBLMA), methacryloyloxy norbornane methacrylate (MNBL), and α-methacryloxy-γ-butyrolactone, among others.

The cycloolefin and the cyclic anhydride monomer are believed to form an alternating polymeric structure, and the amount of the acrylate monomer incorporated into the polymer can be varied to give the optimal lithographic properties. The percentage of the acrylate monomer relative to the cycloolefin/anhydride monomers within the polymer ranges from about 95 mole % to about 5 mole %, preferably from about 75 mole % to about 25 mole %, and most preferably from about 55 mole % to about 45 mole %.

Fluorinated non-phenolic polymers, useful for 157 nm exposure, also exhibit line edge roughness and can benefit from the use of the novel mixture of photoactive compounds described in the present invention. Such polymers are described in WO 00/17712 and WO 00/67072 and incorporated herein by reference. Example of one such polymer is poly(tetrafluoroethylene-co-norbornene-co-5-hexafluoroisopropanol-substituted-2-norbornene.

Polymers synthesized from cycloolefins and cyano containing ethylenic monomers are described in the U.S. patent application Ser. No. 09/854,312, filed May 11, 2001 the contents of which are hereby incorporated herein by reference, may also be used.

The molecular weight of the polymers is optimized based on the type of chemistry used and on the lithographic performance desired. Typically, the weight average molecular weight is in the range of 3,000 to 30,000 and the polydispersity is in the range 1.1 to 5, preferably 1.5 to 2.5.

Other polymers of interest include those found and described in U.S. patent application Ser. No. 10/371,262, filed Feb. 21, 2003, the contents of which are incorporated herein by reference. Still other polymers, such as those disclosed in U.S. patent application Ser. No. 10/440,542, filed May 16, 2003 and titled "Photoresist Composition for Deep UV and Process Thereof", the contents of which are hereby incorporated herein by reference, may also be used.

The solid components of the present invention are dissolved in an organic solvent. The amount of solids in the solvent or mixture of solvents ranges from about 1 weight % to about 50 weight %. The polymer may be in the range of 5 weight % to 90 weight % of the solids and the photoacid generator may be in the range of 1 weight % to about 50 weight % of the solids. Suitable solvents for such photoresists may include a glycol ether derivative such as ethyl cellosolve, methyl cellosolve, propylene glycol monomethyl ether, diethylene glycol monomethyl ether, diethylene glycol monoethyl ether, dipropylene glycol dimethyl ether, propylene glycol n-propyl ether, or diethylene glycol dimethyl ether; a glycol ether ester derivative such as ethyl cellosolve acetate, methyl cellosolve acetate, or propylene glycol monomethyl ether acetate; carboxylates such as ethyl acetate, n-butyl acetate and amyl acetate; carboxylates of di-basic acids such as diethyloxylate and diethylmalonate; dicarboxylates of glycols such as ethylene glycol diacetate and propylene glycol diacetate; and hydroxy carboxylates such as methyl lactate, ethyl lactate, ethyl glycolate, and ethyl-3-hydroxy propionate; a ketone ester such as methyl pyruvate or ethyl pyruvate; an alkoxycarboxylic acid ester such as methyl 3-methoxypropionate, ethyl 3-ethoxypropionate, ethyl 2-hydroxy-2-methylpropionate, or methylethoxypropionate; a ketone derivative such as methyl ethyl ketone, acetyl acetone, cyclopentanone, cyclohexanone or 2-heptanone; a ketone ether derivative such as diacetone alcohol methyl ether; a ketone alcohol derivative such as acetol or diacetone alcohol; lactones such as butyrolactone; an amide derivative such as dimethylacetamide or dimethylformamide, anisole, and mixtures thereof.

Various other additives such as colorants, non-actinic dyes, anti-striation agents, plasticizers, adhesion promoters, dissolution inhibitors, coating aids, photospeed enhancers, additional photoacid generators, and solubility enhancers (for example, certain small levels of solvents not used as part of the main solvent (examples of which include glycol ethers and glycol ether acetates, valerolactone, ketones, lactones, and the like), and surfactants may be added to the photoresist composition before the solution is coated onto a substrate. Surfactants that improve film thickness uniformity, such as fluorinated surfactants, can be added to the photoresist solution. A sensitizer that transfers energy from a particular range of wavelengths to a different exposure wavelength may also be added to the photoresist composition. Often bases are also added to the photoresist to prevent t-tops or bridging at the surface of the photoresist image. Examples of bases are amines, ammonium hydroxide, and photosensitive bases. Particularly preferred bases are trioctylamine, diethanolamine and tetrabutylammonium hydroxide.

The prepared photoresist composition solution can be applied to a substrate by any conventional method used in the photoresist art, including dipping, spraying, and spin coating. When spin coating, for example, the photoresist solution can be adjusted with respect to the percentage of solids content, in order to provide coating of the desired thickness, given the type of spinning equipment utilized and the amount of time allowed for the spinning process. Suitable substrates include silicon, aluminum, polymeric resins, silicon dioxide, doped silicon dioxide, silicon nitride, tantalum, copper, polysilicon, ceramics, aluminum/copper mixtures; gallium arsenide and other such Group III/V compounds. The photoresist may also be coated over antireflective coatings.

The photoresist coatings produced by the described procedure are particularly suitable for application to silicon/silicon dioxide wafers, such as are utilized in the production of microprocessors and other miniaturized integrated circuit components. An aluminum/aluminum oxide wafer can also be used. The substrate may also comprise various polymeric resins, especially transparent polymers such as polyesters.

The photoresist composition solution is then coated onto the substrate, and the substrate is treated (baked) at a temperature from about 70° C. to about 150° C. for from about 30 seconds to about 180 seconds on a hot plate or for from about 15 to about 90 minutes in a convection oven. This temperature treatment is selected in order to reduce the concentration of residual solvents in the photoresist, while not causing substantial thermal degradation of the solid components. In general, one desires to minimize the concentration of solvents and this first temperature. Treatment (baking) is conducted until substantially all of the solvents have evaporated and a thin coating of photoresist composition, on the order of half a micron (micrometer) in thickness, remains on the substrate. In a preferred embodiment the temperature is from about 95° C. to about 120° C. The treatment is conducted until the rate of change of solvent removal becomes relatively insignificant. The film thickness, temperature and time selection depends on the photoresist properties desired by the user, as well as the equipment used and commercially desired coating times. The coated substrate can then be imagewise exposed to actinic radiation, e.g., ultraviolet radiation, at a wavelength of from about 100 nm (nanometers) to about 300 nm, x-ray, electron beam, ion beam or laser radiation, in any desired pattern, produced by use of suitable masks, negatives, stencils, templates, etc.

The photoresist is then subjected to a post exposure second baking or heat treatment before development. The heating temperatures may range from about 90° C. to about 150° C., more preferably from about 100° C. to about 130° C. The heating may be conducted for from about 30 seconds to about 2 minutes, more preferably from about 60 seconds to about 90 seconds on a hot plate or about 30 to about 45 minutes by convection oven.

The exposed photoresist-coated substrates are developed to remove the image-wise exposed areas by immersion in a developing solution or developed by spray development process. The solution is preferably agitated, for example, by nitrogen burst agitation. The substrates are allowed to remain in the developer until all, or substantially all, of the photoresist coating has dissolved from the exposed areas. Developers include aqueous solutions of ammonium or alkali metal hydroxides. One preferred developer is an aqueous solution of tetramethyl ammonium hydroxide. After removal of the coated wafers from the developing solution, one may conduct an optional post-development heat treatment or bake to increase the coating's adhesion and chemical resistance to etching conditions and other substances. The post-development heat treatment can comprise the oven baking of the coating and substrate below the coating's softening point or UV hardening process. In industrial applications, particularly in the manufacture of microcircuitry units on silicon/silicon dioxide-type substrates, the developed substrates may be treated with a buffered, hydrofluoric acid base etching solution or dry etching. Prior to dry etching the photoresist may be treated to electron beam curing in order to increase the dry-etch resistance of the photoresist.

The following examples provide illustrations of the methods of producing and utilizing the present invention. These examples are not intended, however, to limit or restrict the scope of the invention in any way and should not be construed as providing conditions, parameters or values which must be utilized exclusively in order to practice the present invention. Unless otherwise specified, all parts and percents are by weight.

EXAMPLE 1

4-hydroxy-3,5-dimethyl phenyl dimethyl sulphonium nonaflate 15.01 g of 4-Hydroxy-3,5-dimethyl phenyl dimethyl sulphonium chloride, 300 g water, and 23.35 g of potassium perfluorobutane sulfonate in 100 ml acetone were added to a flask. The resulting mixture was stirred for 2 hours at room temperature. The solution was then extracted with chloroform, washed with water, dried over sodium sulphate and filtered. The solution was concentrated and drowned into ether; a precipitate was formed, filtered and dried in the vacuum dryer at less than 40° C., yielding 4-hydroxy-3,5-dimethyl phenyl dimethyl sulphonium nonaflate, 23.9 g (71.9%). The solid product gave the following analytical results: $^1$H NMR (DMSO-d6), 2.35 (s, 6H, $2CH_3$); 3.5 (s, 6H, $2CH_3$); 7.80 (s, 2H, aromatic), mp 98° C.

EXAMPLE 2

4-Acetoxy-3,5-dimethyl phenyl dimethyl sulphonium nonaflate 20.0 g of 4-Hydroxy-3,5-dimethyl phenyl dimethyl sulphonium nonaflate was taken in a round bottom flask, 50 ml acetone and 5.73 g of potassium carbonate were added and then 4.23 g of acetic anhydride was added dropwise at room temperature. The resulting mixture was stirred for 4 hours. The solution was then extracted with chloroform, washed with water, dried over sodium sulphate and filtered. The solution was concentrated and drowned into ether; a precipitate was formed, filtered and dried in the vacuum dryer at less than 40° C., yielding 4-acetoxy-3,5-dimethyl phenyl dimethyl sulphonium nonaflate, 15.0 g (70%). The solid product gave the following analytical results: $^1$H NMR (DMSO-d6), 2.35 (s, 6H, 2CH$_3$); 2.45 (s, 3h, CH$_3$); 3.5 (s, 6H, 2CH$_3$); 7.80 (s, 2H, aromatic), mp 168° C.

EXAMPLE 3

2.0269 g of poly(BNC/MA/MAdMA/GBLMA; mol ratios 1/1/1/1), 0.034 g (30 μmol/g) of triphenylsulfonium nonafluorobutane sulfonate, 0.031 g (30 μmol/g) of 4-acetoxy-3,5-dimethyl phenyl dimethyl sulphonium nonaflate (from Example 2), 0.707 g of 1 weight % propylene glycol monomethyl ether acetate solution of N-(1-Adamantyl) acetamide, and 0.024 g of 10 weight % propylene glycol monomethyl ether acetate solution of a surfactant (FC-430 fluoroaliphatic polymeric ester, supplied by 3M Corporation, St. Paul Minn.) were dissolved in 17.229 g of propylene glycol monomethyl ether acetate to give a photoresist solution; the photoresist solution was filtered through 0.2 μm filter.

EXAMPLE 4

A silicon substrate coated with a bottom antireflective coating (B.A.R.C.) was prepared by spin coating the bottom anti-reflective coating solution (AZ® EXP ArF-1 B.A.R.C. available from Clariant Corporation, Somerville, N.J.) onto the silicon substrate and baking at 175° C. for 60 sec. The B.A.R.C film thickness was 37 nm. The photoresist solution from Example 3 was then coated on the B.A.R.C coated silicon substrate. The spin speed was adjusted such that the photoresist film thickness was 240 nm. The photoresist film was baked at 115° C. for 90 sec. The substrate was then exposed in a 193 nm ISI mini stepper (numerical aperture of 0.6 and coherence of 0.7) using a chrome on quartz binary mask. After exposure, the wafer was post-exposure baked at 130° C. for 90 sec. The imaged photoresist was then developed using a 2.38 weight % aqueous solution of tetramethyl ammonium hydroxide for 30 sec. The line and space patterns were then observed on a scanning electron microscope. The photoresist had a photosensitivity of 13.0 mJ/cm$^2$ and a linear resolution of 0.09 μm.

EXAMPLE 5

8.2086 g of poly(BNC/MA/MAdMA/GBLMA/MNBL; mol ratios 1/1/4/3/1), 0.1385 g (30 μmol/g) of triphenylsulfonium nonafluorobutane sulfonate, 0.1290 g (30 μmol/g) of 4-acetoxy-3,5-dimethyl phenyl dimethyl sulphonium nonaflate (from Example 2), 2.38 g of 1 weight % propylene glycol monomethyl ether acetate solution of N-(1-Adamantyl) acetamide, 0.12 g of 10 weight % propylene glycol monomethyl ether acetate solution of a surfactant (FC-430 fluoroaliphatic polymeric ester, supplied by 3M Corporation, St. Paul Minn.) and 1.83 g of gamma valerolactone were dissolved in 87.1938 g of propylene glycol monomethyl ether acetate to give a photoresist solution; the photoresist solution was filtered through 0.2 μm filter.

EXAMPLE 6

A silicon substrate coated with a bottom antireflective coating (B.A.R.C.) was prepared by spin coating the bottom anti-reflective coating solution (AZ® EXP ArF-1 B.A.R.C. available from Clariant Corporation, Somerville, N.J.) onto the silicon substrate and baking at 175° C. for 60 sec. The B.A.R.C film thickness was 39 nm. The photoresist solution from Example 5 was then coated on the B.A.R.C coated silicon substrate. The spin speed was adjusted such that the photoresist film thickness was 210 nm. The photoresist film was baked at 115° C. for 90 sec. The substrate was then exposed in a 193 nm ISI mini stepper (numerical aperture of 0.6 and coherence of 0.7) using a chrome on quartz binary mask. After exposure, the wafer was post-exposure baked at 130° C. for 90 sec. The imaged photoresist was then developed using a 2.38 weight % aqueous solution of tetramethyl ammonium hydroxide for 30 sec. The line and space patterns were then observed on a scanning electron microscope. The photoresist had a photosensitivity of 13.0 mJ/cm$^2$ and a linear resolution of 0.08 μm.

EXAMPLE 7

16.2755 g of poly(BNC/MA/MAdMA/GBLMA/MNBL; mol ratios 1/1/4/3/1), 0.2746 g (30 μmol/g) of triphenylsulfonium nonafluorobutane sulfonate, 0.3838 g (45 μmol/g) of 4-acetoxy-3,5-dimethyl phenyl dimethyl sulphonium nonaflate (from Example 2), 6.6064 g of 1 weight % propylene glycol monomethyl ether acetate solution of N-(1-Adamantyl) acetamide, 0.24 g of 10 weight % propylene glycol monomethyl ether acetate solution of a surfactant (fluoroaliphatic polymeric ester, supplied by 3M Corporation, St. Paul Minn.) and 3.66 g of gamma valerolactone were dissolved in 172.56 g of propylene glycol monomethyl ether acetate to give a photoresist solution; the photoresist solution was filtered through 0.2 μm filter.

EXAMPLE 8

A silicon substrate coated with a bottom antireflective coating (B.A.R.C.) was prepared by spin coating the bottom anti-reflective coating solution (AZ® EXP ArF-1 B.A.R.C. available from Clariant Corporation, Somerville, N.J.) onto the silicon substrate and baking at 175° C. for 60 sec. The B.A.R.C film thickness was 39 nm. The photoresist solution from Example 7 was then coated on the B.A.R.C coated silicon substrate. The spin speed was adjusted such that the photoresist film thickness was 210 nm. The photoresist film was baked at 115° C. for 90 sec. The substrate was then exposed in a 193 nm ISI mini stepper (numerical aperture of 0.6 and coherence of 0.7) using a chrome on quartz binary mask. After exposure, the wafer was post-exposure baked at 130° C. for 90 sec. The imaged photoresist was then developed using a 2.38 weight % aqueous solution of tetramethyl ammonium hydroxide for 30 sec. The line and space patterns were then observed on a scanning electron microscope. The photoresist had a photosensitivity of 13.0 mJ/cm$^2$ and a linear resolution of 0.09 μm.

EXAMPLE 9

1.6419 g of poly(BNC/MA/MAdMA/GBLMA/MNBL; mol ratios 1/1/4/3/1), 0.0280 g (30 µmol/g) of triphenylsulfonium nonafluorobutane sulfonate, 0.0258 g (30 µmol/g) of 4-acetoxy-3,5-dimethyl phenyl dimethyl sulphonium nonaflate (from Example 2), 0.4801 g of 1 weight % propylene glycol monomethyl ether acetate solution of N-(1-Adamantyl) acetamide, 0.0261 g of 10 weight % propylene glycol monomethyl ether acetate solution of a surfactant (fluoroaliphatic polymeric ester, supplied by 3M Corporation, St. Paul Minn.) and 0.3655 g of gamma valerolactone were dissolved in 17.4374 g of propylene glycol monomethyl ether acetate to give a photoresist solution; the photoresist solution was filtered through 0.2 µm filter.

EXAMPLE 10

A silicon substrate coated with a bottom antireflective coating (B.A.R.C.) was prepared by spin coating the bottom anti-reflective coating solution (AZ® EXP ArF-1 B.A.R.C. available from Clariant Corporation, Somerville, N.J.) onto the silicon substrate and baking at 175° C. for 60 sec. The B.A.R.C film thickness was 39 nm. The photoresist solution from Example 9 was then coated on the B.A.R.C coated silicon substrate. The spin speed was adjusted such that the photoresist film thickness was 240 nm. The photoresist film was baked at 115° C. for 90 sec. The substrate was then exposed in a 193 nm ISI mini stepper (numerical aperture of 0.6 and coherence of 0.7) using a chrome on quartz binary mask. After exposure, the wafer was post-exposure baked at 130° C. for 90 sec. The imaged photoresist was then developed using a 2.38 weight % aqueous solution of tetramethyl ammonium hydroxide for 30 sec. The line and space patterns were then observed on a scanning electron microscope. The photoresist had a photosensitivity of 18.0 mJ/cm$^2$ and a linear resolution of 0.08 µm.

EXAMPLE 11

4-Acetoxy-3,5-dimethyl phenyl dimethyl suliphonium bis-perfluorobutane sulphonimide 3.0 g of 4-Hydroxy-3,5-dimethyl phenyl dimethyl sulphonium chloride, 50 g water, and bis-perfluorobutane sulphonimide acid 13.295 g (50% in water) was added. A precipitate was formed, was filtered, dissolved in chloroform and reprecipitated from ether, yielding 4-hydroxy-3,5-dimethyl phenyl dimethyl sulphonium bis-perfluorobutane sulphonimide (m.p. 84° C.). $^1$H NMR (Acetone-d6), 2.32 (s, 6H, 2 CH$_3$); 3.2 (s, 6H, 2CH$_3$); 7.70 (s, 2H, aromatic); 9.6 (1H, OH).

4.9 g of 4-Hydroxy-3,5-dimethyl phenyl dimethyl sulphonium bis-perfluorobutane sulphonimide was taken in a round bottom flask, 25 g of acetone and 0.89 g of potassium carbonate were added and it was stirred for an hour. Acetic anhydride, 0.66 g, was added drop wise and stirred for 4 hours at room temperature. The reaction mixture was extracted with dichloromethane. Dichloromethane layer was washed with water, dried over sodium sulphate, filtered and the solvent was evaporated under vacuum. Ether was added, 3.3 g of solid was filtered, yielding 4-acetoxy-3,5-dimethyl phenyl dimethyl sulphonium bis-perfluorobutane sulphonimide, mp 68° C. $^1$H NMR (Acetone-d6 2.32 (s, 6H, 2 CH$_3$)), 2.4 (s, 3H, CH$_3$), 3.2 (s, 6H, 2CH$_3$); 7.95 (s, 2H, aromatic).

EXAMPLE 12

1.4381 g of poly(MAdMA/HAdMA/GBLMA; mol ratios 5/2/3); 0.0247 g (30 µmol/g) of triphenylsulfonium nonafluorobutane sulfonate, 0.02347 g (30 µmol/g) of 4-acetoxy-3,5-dimethyl phenyl dimethyl sulphonium bis-perfluorobutane sulphonimide (from Example 11), 0.3519 g of 1 weight % propylene glycol monomethyl ether acetate solution of diisopropylamine, 0.019 g of 10 weight % propylene glycol monomethyl ether acetate solution of a surfactant (fluoroaliphatic polymeric ester, supplied by 3M Corporation, St. Paul Minn.) and 4.059 g propylene glycol monomethyl ether were dissolved in 9.09 g of propylene glycol monomethyl ether acetate to give a photoresist solution; the photoresist solution was filtered through 0.2 µm filter.

EXAMPLE 13

A silicon substrate coated with a bottom antireflective coating (B.A.R.C.) was prepared by spin coating the bottom anti-reflective coating solution (AZ® EXP ArF-1 B.A.R.C. available from Clariant Corporation, Somerville, N.J.) onto the silicon substrate and baking at 175° C. for 60 sec. The B.A.R.C film thickness was 37 nm. The photoresist solution from Example 12 was then coated on the B.A.R.C coated silicon substrate. The spin speed was adjusted such that the photoresist film thickness was 330 nm. The photoresist film was baked at 130° C. for 60 sec. The substrate was then exposed in a 193 nm ISI mini stepper (numerical aperture of 0.6 and coherence of 0.42/0.7, annular illumination) using a chrome on quartz binary mask. After exposure, the wafer was post-exposure baked at 130° C. for 60 sec. The imaged photoresist was then developed using a 2.38 weight % aqueous solution of tetramethyl ammonium hydroxide for 60 sec. The line and space patterns were then observed on a scanning electron microscope. The photoresist had a photosensitivity of 33 mJ/cm$^2$ and a linear resolution of 0.11 µm (1:1).

EXAMPLE 14

Synthesis of poly(1,1,2,3,3-pentafluoro-4-trifluoromethyl-4-hydroxy-1,6-heptadiene) from its methoxymethyl derivative Ten grams of poly(1,1,2,3,3-pentafluoro-4-trifluoromethyl-4-hydroxy-1,6-heptadiene; Asahi Glass Co, LTD, 2-1-2 Marunouchi, Chiyoda-ku Tokyo 100-8305 Japan) protected with 20% of methoxymethyl (MOM) group was dissolved in 30 ml of THF and mixed with 10 ml of trifluoroacetic acid and 7.5 ml of water. This homogeneous solution was stirred overnight at room temperature. After reaction, the solvents were stripped at 50° C. in a rotary evaporator. The residue was dissolved in 30 ml of isopropanol and precipitated in 750 ml of cold water. The precipitate was filtered, washed and dried under vacuum (25" Hg) at 55° C. The isolated yield of the polymer was 98%. NMR analysis confirmed the absence of MOM group.

EXAMPLE 15

Synthesis of tert-butoxycarbonylmethyl protected PPTHH using TMAH.5H$_2$O

PPTHH (4.0 g, 14.81 mmol) from Example 14 was dissolved in 15 ml of THF and to this solution was added solid TMAH.5H2O (0.81 g, 4.44 mmol) while stirring. After 30 minutes of stirring at 25° C., t-butyl bromoacetate (1.74 g, 8.88 mmol) was added to this reaction solution and stirred for another 16 hours at 25° C. After this time, the precipitate formed during the reaction was removed by filtration. The resultant filtrate was then stripped of solvent in a rotary evaporator. The residue was re-dissolved in 20 ml of methanol containing 1.0 g of concentrated HCl. This solution was then precipitated in 200 ml of 15% methanol in water. The precipitate was filtered, washed with distilled water and dried. The polymer was further purified by re-dissolving it in methanol and re-precipitating it in water. After drying under vacuum (25" Hg) at 55° C., the yield of polymer was 92%. The presence of t-butyl (1.48 ppm) and methylene (4.27 ppm) groups were confirmed by $^1$H NMR. The extent of protection with tert-butoxycarbonylmethyl group was found to be 23 mole %.

EXAMPLE 16A 1.15 g of the protected PPTHH from Example 15, 14.44 g propylene glycol monomethyl ether acetate, 1.850 g of a 0.4 weight % solution of tetrabutylammonium acetate in propylene glycol monomethyl ether acetate, and 0.073 g of 4-acetoxy-3,5-dimethyl phenyl dimethyl sulphonium nonaflate (from Example 2) were mixed together in a flask to form a photoresist solution; the photoresist solution was filtered through a 0.2 micron PTFE filter.

EXAMPLE 16B 1.15 g of the protected PPTHH from Example 15, 14.44 g propylene glycol monomethyl ether acetate, 1.850 g of a 0.4 weight % solution of tetrabutylammonium acetate in propylene glycol monomethyl ether acetate, and 0.073 g of 4-methoxy-3,5-dimethyl phenyl dimethyl sulphonium nonaflate (made according to the below following procedure) were mixed together in a flask to form a photoresist solution; the photoresist solution was filtered through a 0.2 micron PTFE filter.

5.0 g (0.023 mole) of 4-hydroxy-3,5-dimethyl phenyl dimethyl sulfonium chloride was placed in a flask equipped with a condenser, a thermometer, and a mechanical stirrer. 45 g of water and 0.92 g of sodium hydroxide were added, and an intense color appeared. Dimethyl sulphate (2.2 ml) was added at room temperature and the mixture was heated at 60° C. for 10 minutes. The solution changed to almost colorless. The heating was stopped after 15 minutes and the solution was cooled to room temperature. 7.78 g of potassium perfluoro butane sulfonate in acetone (50 ml) was added drop wise and mixed for 2 hours. It was extracted with dichloromethane and the dichloromethane layer was washed with water, dried over sodium sulfate, and filtered. The solution was drowned into ether, and the precipitate formed was filtered and dried in the vacuum dryer at less than 40° C. The solid product gave the following analytical results: $^1$H NMR(Acetone-d6), 2.32 (s, 6H, 2CH$_3$); 3.4 (s, 6H, 2CH$_3$); 3.85 (s, 3H, OCH$_3$); 7.78 (s, 2H, aromatic). The absorptivity is 32.82 L/g.cm.

EXAMPLE 16C 1.15 g of the protected PPTHH from Example 15, 14.44 g propylene glycol monomethyl ether acetate, 1.850 g of a 0.4 weight % solution of tetrabutylammonium acetate in propylene glycol monomethyl ether acetate, and 0.073 g of 4-t-butyl acetoxy-3,5-dimethyl phenyl dimethyl sulfonium nonaflate (made according to the below following procedure) were mixed together in a flask to form a photoresist solution; the photoresist solution was filtered through a 0.2 micron PTFE filter.

5.0 g of 4-hydroxy-3,5-dimethyl phenyl dimethyl sulfonium chloride, 100 g water, and 1.0 g of NaOH was added and cool to 0° C. and t-butylbromo acetate (4.46 g) was added, stirred for an hour and 1 hour at room temperature. Then 8.0 g of potassium perfluorobutane sulfonate in acetone were added. The mixture Was stirred for 30 minutes; the solution was extracted with chloroform, washed with water, dried over sodium sulphate and filtered. The solution was drowned into ether; a precipitate was formed, filtered and dried in the vacuum dryer at less than 40° C. The solid product gave the following analytical results: $^1$H NMR (DMSO-d6), 1.48(s, 9H, 3 CH$_3$),2.35 (s, 6H, 2CH$_3$); 3.3 (s, 6H, 2CH$_3$); 7.80 (s, 2H, aromatic), mp 120° C.

EXAMPLE 17

Individual silicone substrates were spin coated (at ~2,200 rpm) with the photoresist solutions of Example 16A, 16B, and 16C and then each substrate was subjected to a post-applied bake of 135° C. for 60 seconds to give a film thickness of the photoresist of about 1350 Å. Each film was then exposed using an Exitech 157 nm small field (1.5×1.5 mm$^2$) mini-stepper (0.6 NA) using a phase-shift mask (σ 0.3) at International SEMATECH in Austin, Tex. The exposed films were subjected to a post-exposure bake of 115° C. for 90 seconds and then developed in 0.26 N tetramethylammonium hydroxide for 30 seconds. An FSI Polaris 2000 track was used to coat, bake, and develop the resist films. A Prometrix interferometer was used to measure resist thickness.

Relative thickness remaining versus dose on a logarithmic scale showed that a photoresist containing an inventive photoactive generator (Example 16A; the inventive photoactive generator of Example 2) had unexpectedly good sensitivity and showed a clearing dose of 35 mJ/cm$^2$ compared to a clearing dose of 85 mJ/cm$^2$ for Example 16B and a clearing dose greater than 100 mJ/cm$^2$ for Example 16C.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

The invention claimed is:

1. 4-Acetoxy-3,5-dimethyl phenyl dimethyl sulphonium nonaflate.

* * * * *